(12) United States Patent
Roifman et al.

(10) Patent No.: US 7,205,113 B2
(45) Date of Patent: Apr. 17, 2007

(54) METHODS OF MODULATION OF THE IMMUNE SYSTEM

(75) Inventors: Chaim M. Roifman, North York (CA); Andrew Freywald, Thornhill (CA); Nigel Sharfe, Toronto (CA); Thomas Grunberger, Toronto (CA); Eyal Gruebaum, Toronto (CA)

(73) Assignee: The Hospital for Sick Children, Toronto (CA)

( * ) Notice: Subject to any disclaimer, the term of this patent is extended or adjusted under 35 U.S.C. 154(b) by 213 days.

(21) Appl. No.: 10/169,520

(22) PCT Filed: Jan. 5, 2001

(86) PCT No.: PCT/CA01/00004

§ 371 (c)(1),
(2), (4) Date: Oct. 26, 2002

(87) PCT Pub. No.: WO01/49743

PCT Pub. Date: Jul. 12, 2001

(65) Prior Publication Data

US 2003/0113328 A1 Jun. 19, 2003

Related U.S. Application Data

(60) Provisional application No. 60/174,710, filed on Jan. 6, 2000.

(51) Int. Cl.
*G01N 33/53* (2006.01)

(52) U.S. Cl. ...................................... 435/7.1; 435/7.24

(58) Field of Classification Search ............. 424/185.1; 514/2, 12; 530/324; 435/7.1, 7.24
See application file for complete search history.

(56) References Cited

FOREIGN PATENT DOCUMENTS

| WO | WO 96/26958 | 9/1996 |
|---|---|---|
| WO | WO 99/17796 | 4/1999 |
| WO | WO 00/30673 | 6/2000 |

OTHER PUBLICATIONS

Freywald et al. The EphB6 receptor inhibits JNK activation in T lymphocytes and modulates T cell receptor-mediated responses. J Biol Chem. Mar. 21, 2003;278(12):10150-6.*
Luo et al. EphB6-null mutation results in compromised T cell function. J Clin Invest. Dec. 2004;114(12):1762-73.*
Kuntz ID. Structure-based strategies for drug design and discovery. Science. Aug. 21, 1992;257(5073):1078-82.*
Meima et al. Lerk2 (ephrin-B1) is a collapsing factor for a subset of cortical growth cones and acts by a mechanism different from AL-1 (ephrin-A5). Mol Cell Neurosci. 1997;9(4):314-28.*
Miller et al. Ligand binding to proteins: the binding landscape model. Protein Sci. Oct. 1997;6(10):2166-79.*
Abraham, C., Griffith, J. & Miller, J. The dependence for leukocyte function-associated antigen-1/ICAM-1 interactions in T cell activation cannot be overcome by expression of high density TCR ligand. *J. Immunol* 162, 4399-405 (1999).
Adams, R.H. et al. Roles of ephrinB ligands adn EphB receptors in cardiovascular development: demarcation of arterial/venous domains, vascular morphogenesis, and sprouting angiogenesis. *Genes Dev* 13, 295-306 (1999).
Aggarwal, S. S. Gollapudi, S. Gupta, *J Immunol* 162,2154-61 (1999).
Alderson, M. R., et al., *J Exp Med* 181,71-7 (1995).
Baker, S. J., E. P. Reddy, *Oncogene* 17,3261-70 (1998).
Bartley TD, Hunt RW, Welcher AA, Boyle WJ, Parker VP, Lindberg RA, Lu HS, Colombero AM, Elliott RL, Guthrie BA, et al. *Nature* Apr. 7, 1994; 368 (6471): 558-60 B61 is a ligand for the ECK receptor protein-tyrosine kinase.
Becker, E. et al. Nck-interacting Ste20 kinase couples Eph receptors to c-Jun N-terminal kinase and integrin activation. *Mol Cell Biol* 20,1537-45 (2000).
Blake, T. J., Shapiro, M., Morse, H.C.d. & Langdon, W. Y. The sequences of the human and mouse c-cb1 proto-oncogens show v-cb1 was generated by a large truncation encompassing a proline-rich domain and a leucine zipper-like motif. *Oncogene* 6,653-7 (1991).
Blechman JM, Lev S, Brizzi MF, Leitner O, Pegoraro L, Givol D, Yarden Y, *Biol Chem* Feb. 25, 1993; 268 (6): 4399-406. Soluble c-kit proteins and antireceptor monoclonal antibodies confine the binding site of the stem cell factor.
Blechman JM, Lev S, Barg J, Eisenstein M, Vaks B, Vogel Z, Givol D, Yarden Y Cell Jan. 13, 1995;80(1):103-13. The fourth immunoglobulin domains of the stem cell factor receptor couples ligand binding to signal transduction.
Bleijs, D. A., de Waal-Malefyt, R., Figdor, C.G. & van Kooyk, Y. Co-stimulation of T cells results in distinct IL-10 and TNF-alpha cytokine profiles dependent on binding to ICAM-1, ICAM-2, ICAM-3. *Eur F Inimunol* 29, 2248-58, (1999).
Boehme, S.A., L. Zheng, M.J. Lenardo, J Immunol 155, 1703-12 (1995).

(Continued)

*Primary Examiner*—Maher M. Haddad
(74) *Attorney, Agent, or Firm*—Jagtiani + Guttag

(57) ABSTRACT

Manipulation of the EphB6 receptor and its active Eph partners allow for regulation of T cell responses, including TCR signaling, T cell proliferation, and induction of T cell death. Methods of modulating EphB6 are described as well as various therapeutic applications.

3 Claims, 15 Drawing Sheets

OTHER PUBLICATIONS

Bohme, B. et al. Cell-cell adhesion mediated by binding a membrane-anchored ligand LERK-2 to the EPH-related receptor human embryonal kinase 2 promotes tyrosine kinase activity. *Journal of Biological Chemistry* 271, 24747-52 (1996).

Bonita, D.P., Miyake, S., Lupher, M.L., Jr., Langdon, W.Y. & Band, H. Phosphotyrosine binding domain-dependent upregulation of the platelet-derived growth factor receptor alpha signaling cascade by transforming mutants of Cb1: implications for Cb1's function and oncogenicity. *Mol Cell Biol* 17, 4597-610 (1997).

Brambilla, R. et al. Membrane-bounded LERK2 ligand can signal through three different Eph-related receptor tyrosine kinases. *Embo Journal* 14, 3116-26 (1995).

Chambers, C.A. & Allison, J.P. Co-stimulation in T cell responses. *Curr Opin Immunol* 9, 396-404 (1997).

Choi, S. & Park, S. Phosphorylation at Tyr-838 in the kinase domain of EphA8 modulates Fyn binding to the Tyr-615 site by enhancing tyrosine kinase activity. *Oncogene* 18, 5413-5422 (1999).

Chong, L.D., E.K. Park, E. Latimer, R. Friesel, I.O. Daar, Mol Cell Biol 20, 724-34 (2000).

Chou, Y.H. & Hayman, M.J. Characterization of a member of the immunoglobulin gene superfamily that possibly represents an additional class of growth factor receptor. *Proc Natl Acad Sci USA* 88, 4897-901 (1991).

Ciossek, T. & Ullrich, A. Identification of Elf-1 and B61 as high affinity ligands for the receptor tyrosine kinase MDK1. *Oncogene* 14, 35-43 (1997).

Ciossek, T. et al. Eph receptor-ligand interactions are necessary for guidance of retinal ganglion cell axons in vitro. *Eur J Neurosci* 10, 1574-80 (1998).

Cross, J.V., et al., [J] Biol Chem 274, 31150-4 (1999).

Daniel, T.O. et al. ELK and LERK-2 in developing kidney and microvascular endothelial assembly. *Kidney International Supplement* (1996).

Davis, S. et al. Ligands for EPH-related receptor tyrosine kinases that require membrane attachment or clustering for activity. *Science* 266, 816-9 (1994).

Dhein, J.,H. Walczak, C. Baumler, K.M. Debatin, P.H. Krammer, Nature 373,438-41 (1995).

Drescher, U. et al. In vitro guidance of retinal ganglion cell axons by RAGS, a 25 kDa tectal protein related to ligands for Eph receptor tyrosine kinases. *Cell* 82, 359-70 (1995).

Drescher, U. The Eph family in the patterning of neural development. *Current Biology* 7 (1997).

Durbin, L., et al. Development 127, 1703-13 (2000).

Dustin, M.L. & Shaw, A.S. Costimulation: building an immunological synapse. *Science* 283, 649-50 (1999).

Dutting, D., C. Handwerker, U. Drescher, Dev Biol 216,297-311 (1999).

Birgbauer, E., C. A. Cowan, D. W. Sretavan, M. Henkemeyer, Development 127,1231-41 (2000).

Ellis, C. et al. A juxtamembrane autophosphorylation site in the Eph family receptor tyrosine kinase, Sek, mediates high affinity interactions with p59fyn. *Oncogene* 12, 1727-36 (1996).

Flanagan, J.G. & Vanderhaeghen, P. The ephrins and Eph receptors in neural development. *Annu Rev Neurosci* 21, 309-45 (1998).

Fournel, M., Davidson, D., Weil, R. & Veillette, A. Association of tyrosine protein kinase Zap- 70 with the protooncogene product p120C-cb1 in T lymphocytes. *J Exp Med* 183, 301-6 (1996).

Friedman, G.C. & O'Leary, D.D. Eph receptor tyrosine kinases and their ligands in neural development. *Current Opinion in Neurobiology* 6, 127-33 (1996).

Gale, N.W. et al. Eph receptors and ligands comprise two major specificity subclasses and are reciprocally compartmentalized during enbryogenesis. *Neuron* 17, 9-19, (1996).

Gao, P.P., Yue, Y., Cerretti, D.P., Dreyfus, C. & Zhou, R. Ephrin-dependent growth and pruning of hippocampal axons. *Proc Natl Acad Sci USA* 96, 4073-7 (1999).

Greginat, J., Bossi, G., Bender, J.R. & Pardi, R. Anchorage dependence of mitogen-induced G1 to S transition in primary T lymphocytes. *J Immunol* 162, 5085-93 (1999).

Grakoui, A. et al. The immunological synapse: a molecular machine controlling T cell activation. *Science* 285, 221-7 (1999).

Gurniak, C.B. & Berg, L.J. A new member of the Eph family of receptors that lacks protein tyrosine kinase activity. *Oncogene* 13, 777-86 (1996).

Hattori, M., M. Osterfield, J.G. Flanagan, Science 289, 1360-5 (2000).

Helbling, P.M., D.M. Saulnier, A. W. Brandli, Development 127, 269-78 (2000).

Hock, B. et al. Tyrosine-614, the major autophosphorylation site of the receptor tyrosine kinase HEK2, functions as multi-docking site for SH2-domain mediated interactions. *Oncogene* 17, 255-260 (1998).

Holland, S.J. et al. Juxtamembrane tyrosine residues couple the Eph family receptor EphB2/Nuk to specific SH2 domain proteins in neuronal cells. *Embo J* 16, 3877-88 (1997).

Holsinger, L.J. et al. Defects in actin-cap information in Vav-deficient mice implicate an actin requirement for lymphocyte signal transduction. *Curr Biol* 8, 563-72 (1998).

Honegger, A.M., Schmidt, A., Ullrich, A. & Schlessinger, J. Evidence for epidermal growth factor (EGF)-induced intermolecular autophosphorylation of the EGF receptors in living cells. *Molecular & Cellular Biology* 10, 4035-44 (1990).

Hornberger, M.R. et al. Modulation of EphA receptor function by coexpressed ephrinA ligands on retinal.ganglion cell axons. *Neuron* 22, 731-42 (1999).

Hopp, T.P. & Woods, K.R. Prediction of protein antigenic determinants from amino acid sequences. *Proc Natl Acad Sci USA* 78, 3824-8 (1981).

Hovens, C.M. et al. RYK, a receptor tyrosine kinase-related molecule with unusual kinase domains motifs. *Proc Natl Acad Sci USA* 89, 11818-22 (1992).

Hsueh, Y.P. & Sheng, M. Eph receptors, ephrins, and PDZs gather in neuronal synapses. *Neuron* 21, 1227-9 (1998).

Hunter, S., Burton, E.A., Wu, S.C. & Anderson, S.M. Fyn associates with Cb1 and phosphorylates tyrosine 731 in Cb1, a binding site for phosphatidylinositol 3-kinase. *J Biol Chem* 274, 2097-106 (1999).

Huynh-Do, U. et al. Surface densities of ephrin-B1 determine EphBL-coupled activation of cell attachment through alphavbeta3 and alpha5beta1 integrins. *Embro J* 18, 2165-73 (1999).

Janeway, C.A., Jr. & Bottomly, K. Signals and signs for lymphocyte responses. *Cell* 76, 275-85 (1994).

Jongeward, G.D., Clandinin, T.R. & Sternberg, P.W. sli-1, a negative regulator of let-23-mediated signaling of *C. elegans*. *Genetics* 139, 1553-66 (1995).

Ju, S.T., et al., Nature 373,444-8 (1995).

Kashles, O., Yarden, Y., Fischer, R., Ullrich, A. & Schlessinger, J.A dominant negative mutation suppresses the function of normal epidermal growth factor receptors by heterodimerization. *Molecular & Cellular Biology* 11, 1454-63 (1991).

Kavanaugh, W.M., Turck, C.W. & Williams, L.T. PTB domain binding to signaling proteins through a sequence motif containing phosphotyrosine. *Science* 268, 1177-9 (1995).

Kelman, Z., Simon-Chazottes, D., Guenet, J.L. & Yarden, Y. The murine vik gene (chromosome 9) encodes a putative receptor with unique protein kinase mofits. *Oncogene* 8, 37-44 (1993).

Kim, H.H., Sierke, S.L. & Koland, J.G. Epidermal growth factor-dependent association of phosphatidylinositol 3-kinase with the erbB3 gene product. *J Biol Chem* 269, 24747-55 (1994).

Koch, C.A., Anderson, D., Moran, M.F., Ellis, C. & Pawson, T. SH2 and SH3 domains: elements that control interactions of cytoplasmic signalling proteins. *Science* 252,668-74 (1991).

Kong, G. et al. Distant tyrosine phosphorylation sites in ZAP-70 mediate activation and negative regulation of antigen receptor function. *Mol Cell Biol* 16, 5026-35 (1996).

Kozlosky, C.J. et al. Ligands for the receptor tyrosine kinases hek and elk: isolation of cDNAs encoding a family of proteins. *Oncogene* 10, 299-306 (1995).

Krull, C.E. et al. Interactions of Eph-related receptors and ligands confer rostrocaudal pattern to trunk neural crest migration. *Current Biology* 7, 571-80 (1997).

Lee, P.S. et al. The Cbl protooncoprotein stimulates CSF-1 receptor multiubiquitination and endocytosis, and attenuates macrophage proliferation. *Embo J* 18, 3616-28 (1999).

Lev S, Blechman J, Nishikawa S, Givol D, Yarden Y. Mol Cell Biol Apr. 1993; 13 (4): 2224-34. Interspecies molecular chimeras of kit help define the binding site of the stem cell factor.

Levkowitz, G. et al. c-Cbl/Sli-1 regulates endocytic sorting and ubiquitination of the epidermal growth factor receptor. *Genes Dev* 12, 3663-74 (1998).

Levkowitz, G. et al. Coupling of the c-Cbl protooncogene product to ErbB-1/EGF-receptor but not to other ErbB proteins. *Oncogene* 12, 1117-25 (1996). 98.

Hershko, A. & Ciechanover, A. The ubiquitin system. *Annu Rev Biochem* 67, 425-79 (1998).

Lupher, M.L., Jr., Reedquist, K.A., Miyake, S., Langdon, W.Y. & Band, H. A novel phosphotyrosine-binding domain in the N-terminal transforming region of Cbl interacts directly and selectively with ZAP-70 in T cells. [J] Biol Chem 271, 24063-8 (1996).

Lupher, M. L., Jr., Songyang, Z., Shoelson, S. E., Cantley, L. C. & Band, H. The Cbl phosphotyrosine-binding domain selects a D(N/D)XpY motif and binds to the Tyr292 negative regulatory phosphorylation site of ZAP-70. *J Biol Chem* 272, 33140-4 (1997).

Lupher, M.L., Jr. et al. Cbl-mediated negative regulation of the Syk tyrosine kinase. A critical role for Cbl phosphotyrosine-binding domain binding to Syk phosphotyrosine 323. *J Biol Chem* 273, 35273-81 (1998).

Mary, F. et al. Modulation of TCR signaling by beta 1 integrins: role of the tyrosine phosphatase SHP-1. *Eur J Immunol* 29, 3887-97 (1999).

Matsuoka, H. et al. Expression of a kinase-defective Eph-like receptor in the normal human brain. *Biochemical & Biophysical Research Communications* 235, 487-92 (1997).

Mege, D. et al. Mutation of tyrosines 492/493 in the kinase domain of ZAP-70 affects multiple T-cell receptor signaling pathways. *J Biol Chem* 271, 32644-52 (1996).

Meima, L. et al. AL-1-induced growth cone collapse of rat cortial neurons is correlated with REK7 expression and rearrrangement of the actin cytoskeleton, *Eur J Neurosci* 9, 177-88 (1997).

Meima, L., Moran, P., Matthews, W. & Caras, I. W. Lerk2 (ephrin-B1) is a colllapsing factor for a subset of cortical growth cones and acts by a mechanism different from AL-1 (ephrin-A5). *Mol Cell Neurosci* 9, 314-28 (1997).

Mellitzer, G., Xu, Q. & Wilkinson, D.G. Eph receptors and ephrins restrict cell intermingling and communication. *Nature* 400, 77-81 (1999).

Maio, H., Burnett, E., Kinch, M; Simon, E. & Wang, B. Activation of EphA2 kinase suppresses integrin function and causes focal-adhesion-kinase dephosphorylation. *Nat Cell Biol* 2,62-9 (2000).

Miyake, S., Lupher, M.L., Jr., Druker, B. & Band, H. The tyrosine kinase regulator Cbl enhances the ubiquitination and degradation of the platelet-derived growth factor receptor alpha. *Proc Natl Acad Sci USA* 95, 7927-32 (1998).

Monschau, B. et al. Shared and distinct functions of RAGS and ELF-1 in guiding retinal axons. *Embo Journal* 16, 1258-67 (1997).

Munthe Else et al. Ephrin-B2 is a candidate ligand for the EPH receptor EphB6, vol. 94, No. 10, Suppl. 1 Part 1, Nov. 15, 1999.

Nakamoto, M. et al. Topographically specific effects of ELF-1 on retinal axon guidance in vitro and retinal axon mapping in vivo. *Cell* 86, 755-66 (1996).

Noel, P.J., L.H. Boise, J.J. Green, C.B. Thompson, *J Immumol* 157, 636-42 (1996).

O'Leary, D.D. & Wilkinson, D.G. Eph receptors and ephrins in neural development. *Curr Opin Neurobiol* 9, 65-73 (1999).

Ota, Y. & Samelson, L.E. The product of the proto-oncogene c-cbl: a negative regulator of the Syk Tyrosine kinase. *Science* 276, 418-20 (1997).

Paul, S.R. et al. Molecular cloning of the cDNA encoding a receptor tyrosine kinase-related molecule with a catalytic region homologous to c-met. *Int J Cell Cloning* 10, 309-14 (1992).

Pandey, A., Shao, H., Marks, R.M., Polverini, P.J. & Dixit, V.M. Role of B61, the ligand for the Eck receptor tyrosine kinase, in TNF-alpha-induced angiogenesis, *Science* 268, 567-9 (1995).

Park, S. & Sanchez, M.P. The Eek receptor, a member of the Eph family of tyrosine protein kinases, can be activated by three different Eph family ligands. *Oncogene* 14, 533-42 (1997).

Pasquale, E.B. The Eph family of receptors. *Current Opinion in Cell Biology* 9, 608-15 (1997).

Pinkas, K.R. et al. Diversification of Neu differentiation factor and epidermal growth factor signaling by combinatorial receptor interactions. *Embo Journal* 15, 2452-67 (1996).

Roulston A.,C. Reinhard, P. Amiri, L.T. Williams, *J Biol Chem* 273, 10232-9 (1998).

Russell, J.H., B. Rush, C. Weaver, R. Wang, *Proc Natl Acad Sci USA* 90, 4409-13 (1993).

Sabapathy, K., et al., Curr Biol 9, 116-25 (1999).

Sakano, S. et al. Characterization of a ligand for receptor protein-tyrosine kinase HTK expressed in immature hematopoietic cells. *Oncogene* 13, 813-22 (1996).

Shimoyana, M. et al., *Growth Factors*, 18, 63-78 (2000).

Smith, A., Robinson, V., Patel, K. & Wilkinson, D.G. The EphA4 and EphB1 receptor tyrosine kinases and ephrin-B2 ligand regulate targeted migration of branchial neural crest cells. *Current Biology* 7, 561-70 (1997).

Snapper, S.B., et al. Wiskott-Aldrich syndrome protein-deficient mice reveal a role for WASP in T but not B cell activation. *Immunity* 9, 81-91 (1998).

Songyang, Z. et al. SH2 domains recognize specific phosphopeptide sequences. *Cell* 72, 767-78 (1993).

Stacker, S. A. et al. Molecular cloning and chromosomal localisation of the human homologue of a receptor related to tyrosine kinases (RYK). *Oncogene* 8, 1347-56 (1993).

Takahashi, T., et al., Cell 76,969-76 (1994).

Tamagnone, L. et al. The human ryk cDNA sequence predicts a protein containing two putative transmembrane segments and a tyrosine kinase catalytic domain. *Oncogene* 8, 2009-14 (1993).

Thien, C.B. & Langdon, W.Y. EGF receptor binding a transformation by v-cbl is ablated by the introduction of a loss-of-function mutation for the *Caenorhabditis elegans* sli-1 gene. *Oncogene* 14, 2239-49 (1997).

Thien, C.B., Bowtell, D.D. & Langdon, W.Y. Perturbed regulation of ZAP-70 and sustained tyrosine phosphorylation of LAT and SLP-76 in c-Cbl-deficient thymocytes. *J Immunol* 162, 7133-9 (1999).

Ticchioni, M. et al. Suppressive effect of T cell proliferation via the CD29 molecule. The CD29 mAb 1 "K20" decrease diacylglycerol and phosphatidic acid levels in activated T cells. *J. Immunol* 151, 119-27 (1993).

Thoma, B., M. Grell, K. Pfizenmaier, P. Schuerich, J Exp Med 172, 1019-23 (1990).

Torres, R. et al. PDZ proteins bind, cluster, and synaptically colocalize with Eph receptors and their ephrins ligands [see comments]. *Neuron* 21, 1453-63 [(1998)].

Tsygankov, A.Y., Mahajan, S., Fincke, J.E. & Bolen, J.B. Specific association of tyrosine-phosphorylated c-Cbl with Fyn tyrosine kinase in T cells. *J Biol Chem* 271, 27130-7 (1996).

Ueno, H., Colbert, H., Escobedo, J.A. & Williams, L.T. Inhibition of PDGF beta receptor signal transduction by coexpression of a truncated receptor. *Science* 252, 844-8 (1991).

Utting, O., Teh, S.J. & Teh, H.S. T cells expressing receptors of different affinity for antigen ligands reveal a unique role for p59fyn in T cell development and optimal stimulation of T cells by antigen. *J Immunol* 160, 5410-9 (1998).

Valitutti, Dessing, M., Aktories, K., Gallati, H. & Lanzavecchia, A. Sustained signaling leading to T cell activation results from prolonged T cell receptor occupancy. Role of T cell actin cytoskeleton. *J Exp Med* 181, 577-84 [(1995).].

van der Geer, P., Hunter, T. & Lindberg, R.A. Receptor protein-tyrosine kinases and their signal transduction pathways. *Annual Review of Cell Biology* 10, 251-337 (1994).

van Leeuwen, J.E., Paik, P.K. & Samelson, L.E. The Oncogenic 70Z Cbl Mutations Blocks the Phosphotyrosine Binding Domain-Dependent Negative Regulation of ZAP-70 by c-Cbl in Jurkat T Cells. *Mol Cell Biol* 19, 6652-6664 (1999).

Van Ostade, X., et al., Nature 361,266-9 (1993).

Viola, A., Schroeder, S., Sakakibara, Y. & Lanzavecchia, A. T lymphocyte costimulation mediated by reorganization of membrane microdomains [see comments]. *Science* 283, 680-2 (1999).

Vivinus-Nebot, M. et al. Laminin 5 in the human thymus: control of T cell proliferation via α6β4 integrins. *J Cell Biol* 144, 563-74 (1999).

Watanabe-Fukunaga, R., C.I. Brannon, N.G. Copeland, N.A. Jenkins, S. Nagata, Nature 356, 314-7 (1992).

Wang, H.U., Chen, Z. F. & Anderson, D. J. Molecular distinction and angiogenic interaction between embryonic arteries and veins revealed by ephrin-B2 and its receptor Eph-B4. *Cell* 93, 741-53 (1998).

Wange, R.L. et al. Activating and inhibitory mutations in adjacent tyrosines in the kinase domain of ZAP-70. *J Biol Chem* 270, 18730-3 (1995).

Waterman, H., Alroy, I., Strano, S., Seger, R. & Yarden, Y. The C-terminus of the kinase-defective neuregulin receptor ErbB-3 confers mitogenic superiority and dictates endocytic routing. *Embo J* 18, 3348-58 (1999).

Winslow, J.W. et al. Cloning of AL-1, a ligand for an Eph-related tyrosine kinase receptor involved in axon bundle formation. *Neuron* 14, 973-81 (1995).

Wu, J. et al. Function and signaling of an Eph family receptor tyrosine kinase EphB6 in lymphocytes. *Faseb Journal*, vol. 14, No. 6, Apr. 20, 2000 p. A1155.

Wulfing, C. & Davis, M.M. A receptor/cytoskeletal movement triggered by costimulation during T cell activation. *Science* 282, 2266-9 (1998).

Wulfing, C., Sjaastad, M.D. & Davis M.M. Visualizing the dynamics of T cell activation: intracellular adhesion molecule 1 migrates rapidly to the T cell/B cell interace and acts to sustain calcium levels. *Proc Natl Acad Sci USA* 95, 6302-7 (1998).

Xu, Q., Mellitzer, G., Robinson, V. & Wilkinson, D. G. In vivo cell sorting in complementary segmental domains mediated by Eph receptors and ephrins. *Nature* 399, 267-71 (1999).

Yarden, Y. & Schlessinger, J. Epidermal growth factor induces rapid, reversible aggregation of the purified epidermal growth factor receptor. *Biochemistry* 26, 1443-51 (1987).

Yarden, Y. & Schlessinger, J. Self-phosphorylation of epidermal growth factor receptor: evidence for a model of intermolecular allosteric activation. *Biochemistry* 26, 1434-42 (1987).

Yue, Y. et al. Specification of distinct dopaminergic neural pathways: roles of the Eph family receptor EphB1 and ligand ephrin-B2. *J Neurosci* 19, 2090-101 (1999).

Zisch, A.H. & Pasquale, E.B. The Eph family: a multitude of receptors that mediate cell recognition signals. *Cell & Tissue Research* 290, 217-26 (1997).

Zheng, L. et al., Nature 377, 348-51 (1995).

Zhou, R. The Eph family receptors and ligands. [Review] [181 refs]. *Pharmacology & Therapeutics* 77, 151-81 (1998).

Zou, J.X. et al. An Eph receptor regulates integrin activity through R-Ras. *Proc Natl Acad Sci USA* 96, 13813-8 (1999).

\* cited by examiner

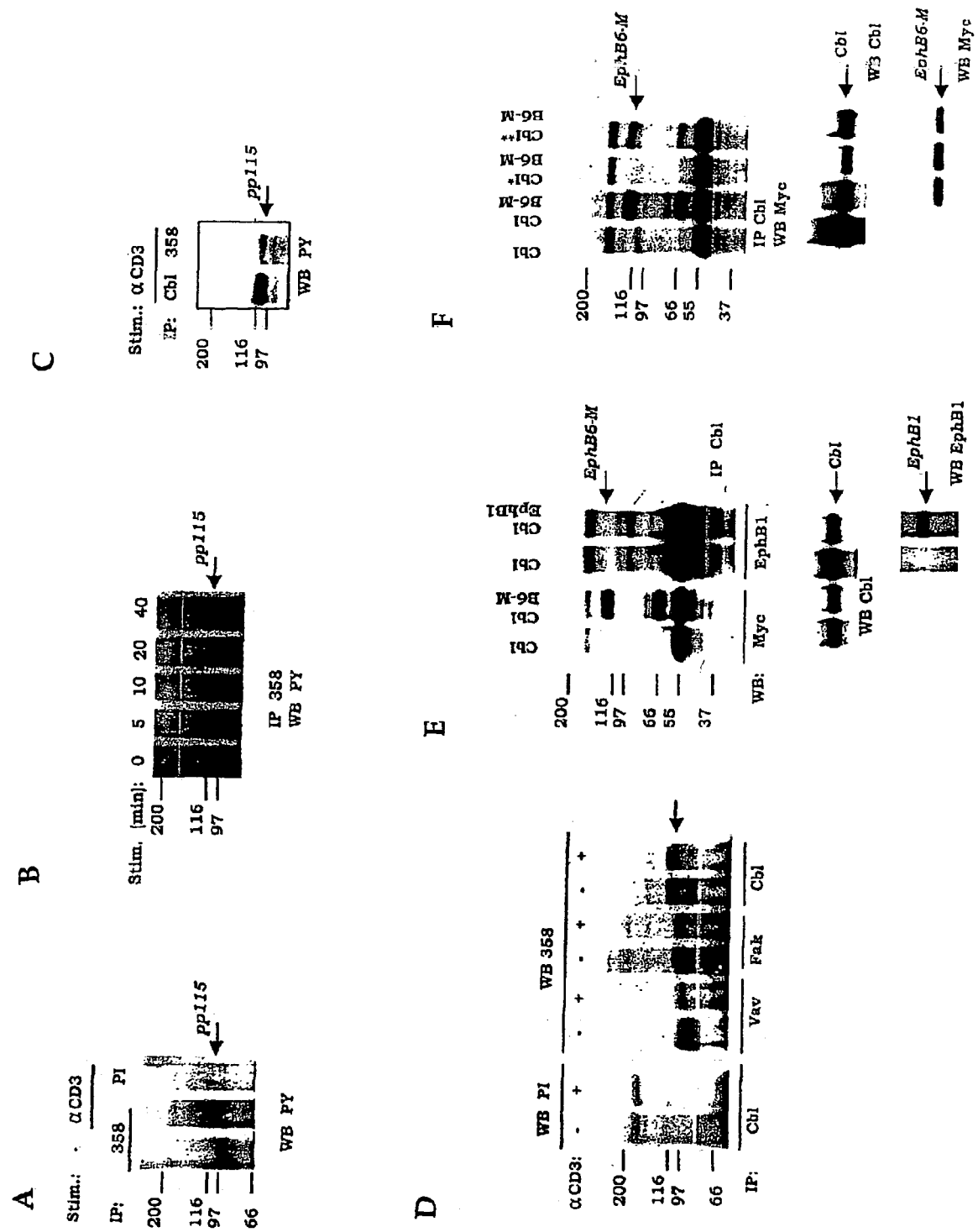
FIGURE 4A-F

FIGURE 5A-B
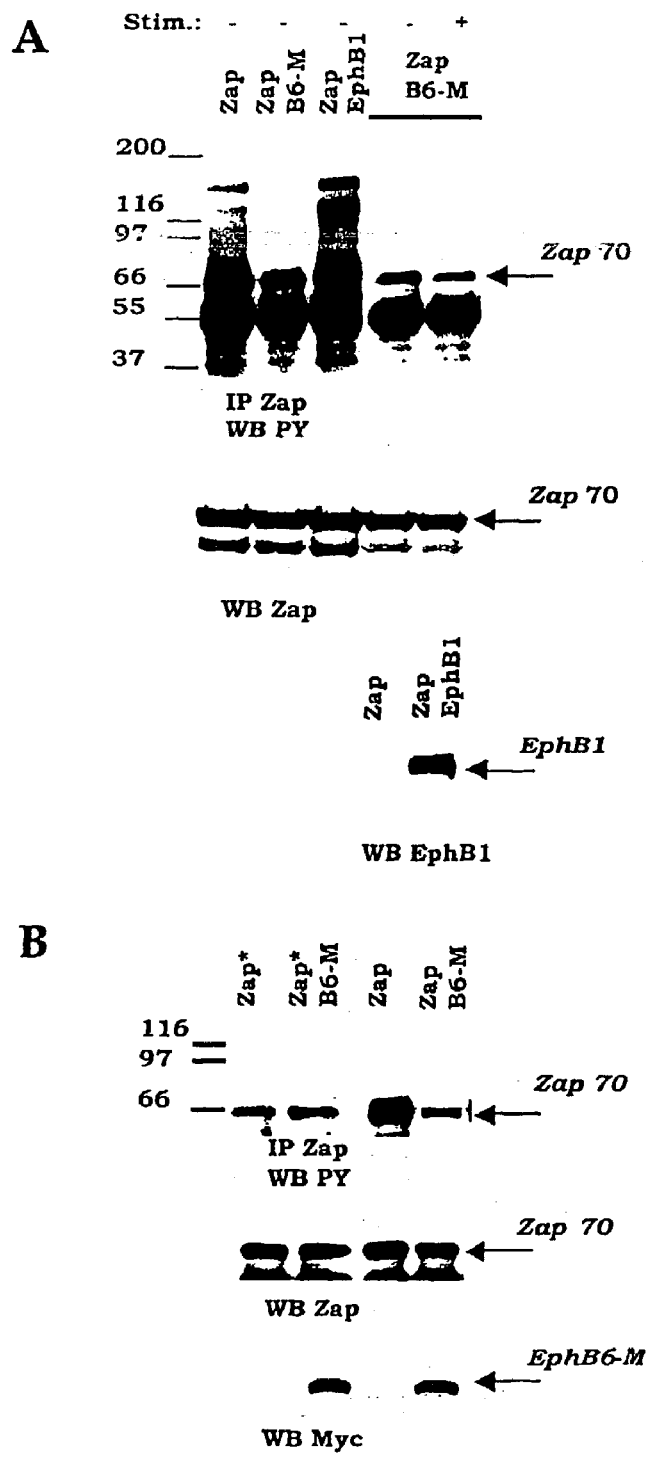

FIGURE 5C-F
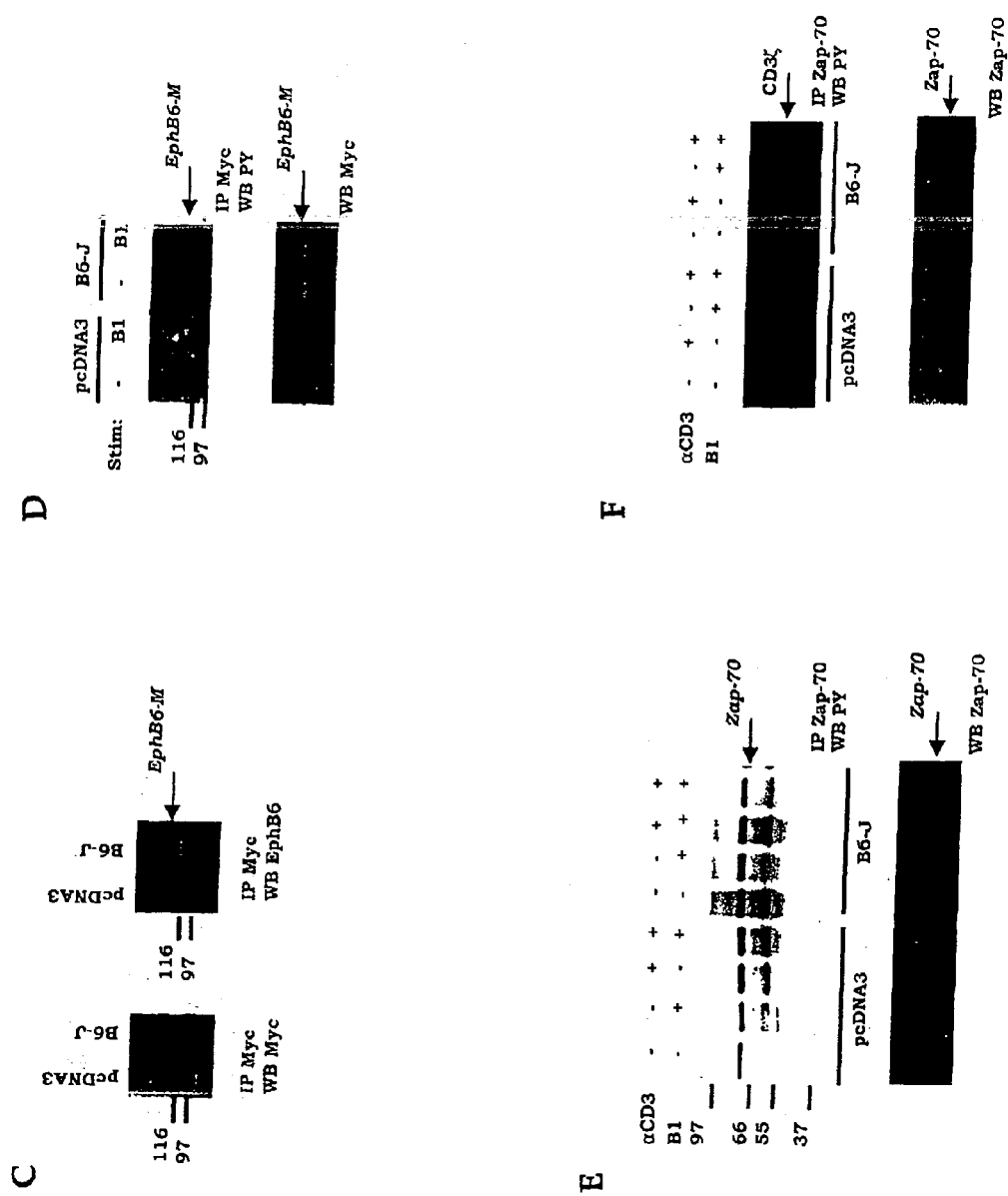

FIGURE 6A-B
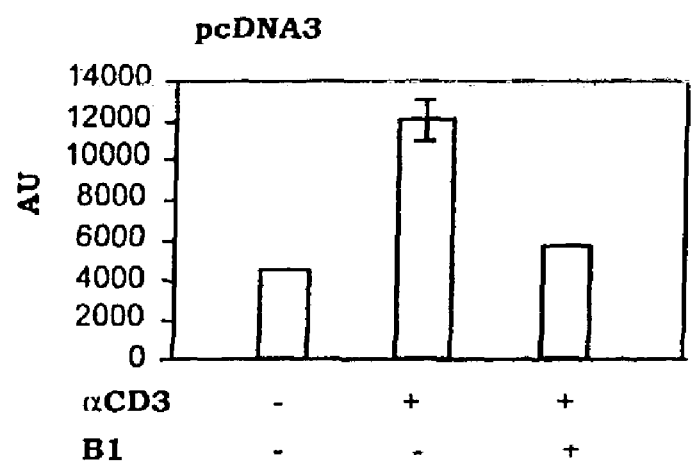
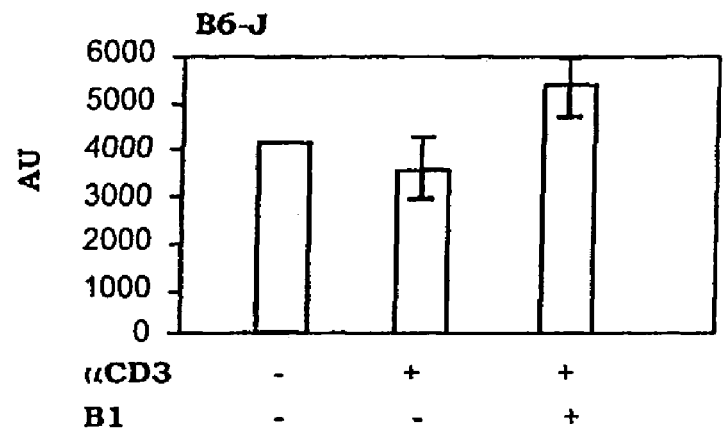

FIGURE 7A-B
A
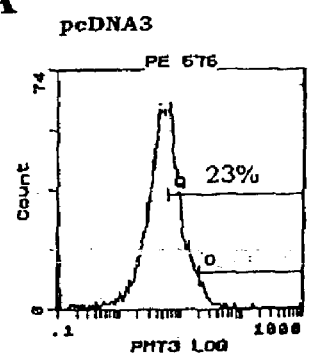
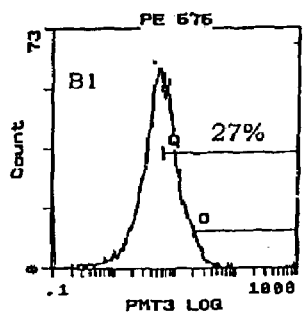
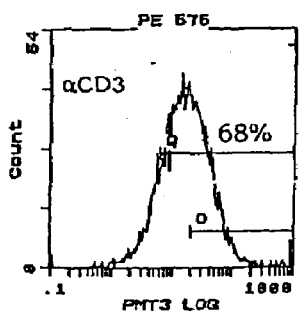
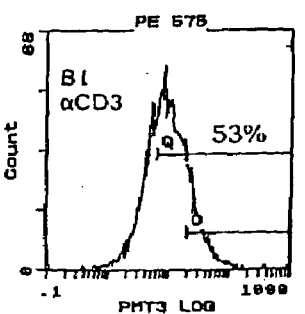
B
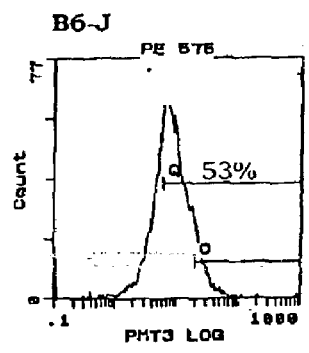
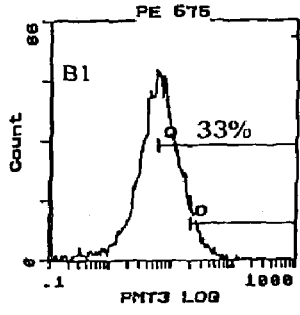
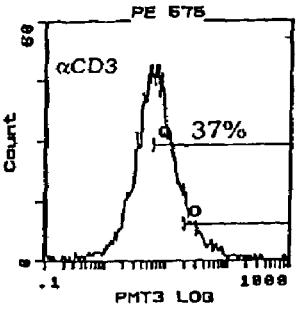
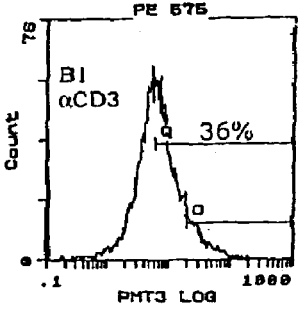

FIGURE 8A-B
A
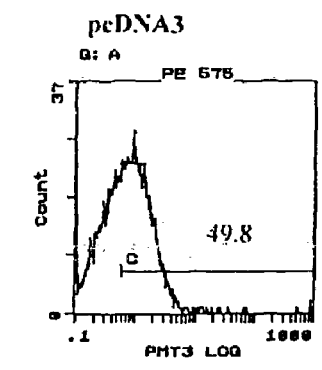
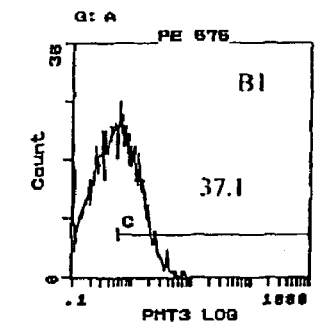
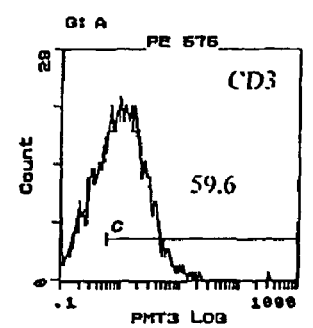
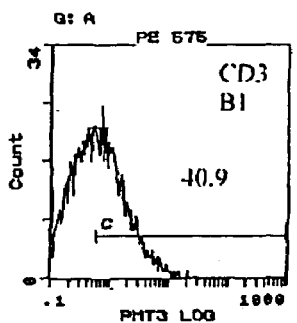
B
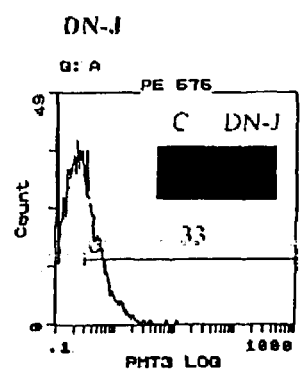
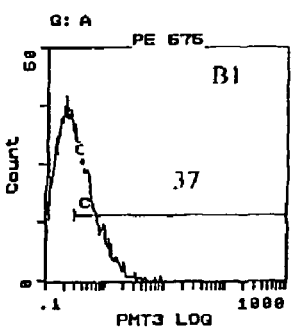
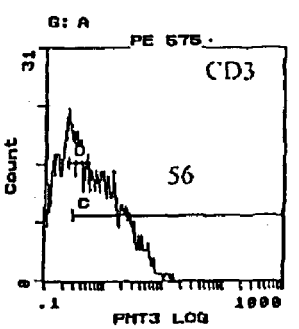
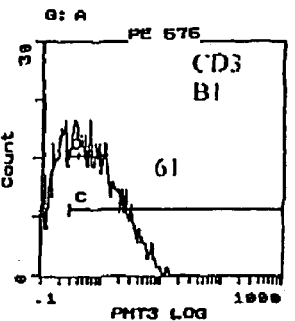

FIGURE 9A-B
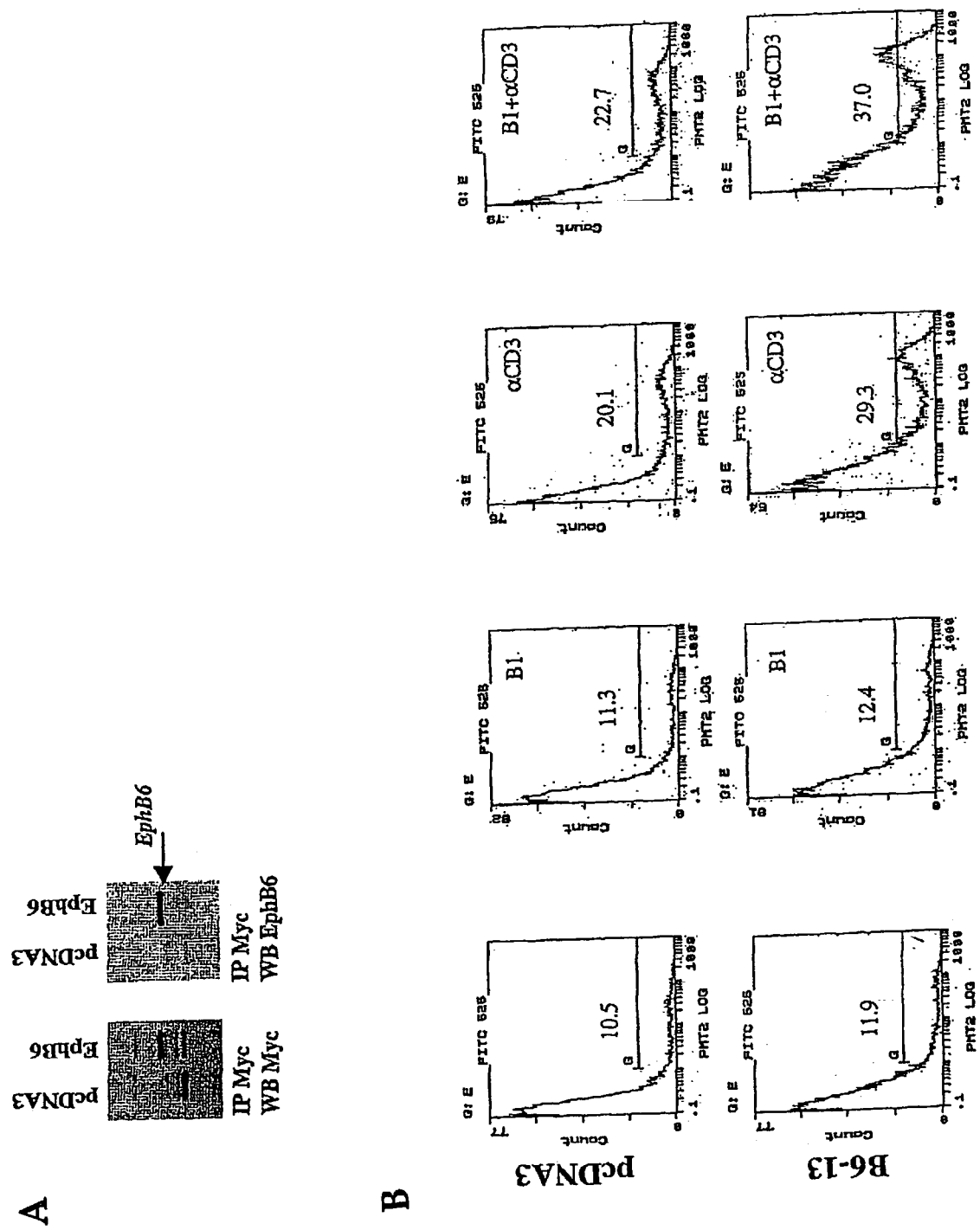

FIGURE 11A-B
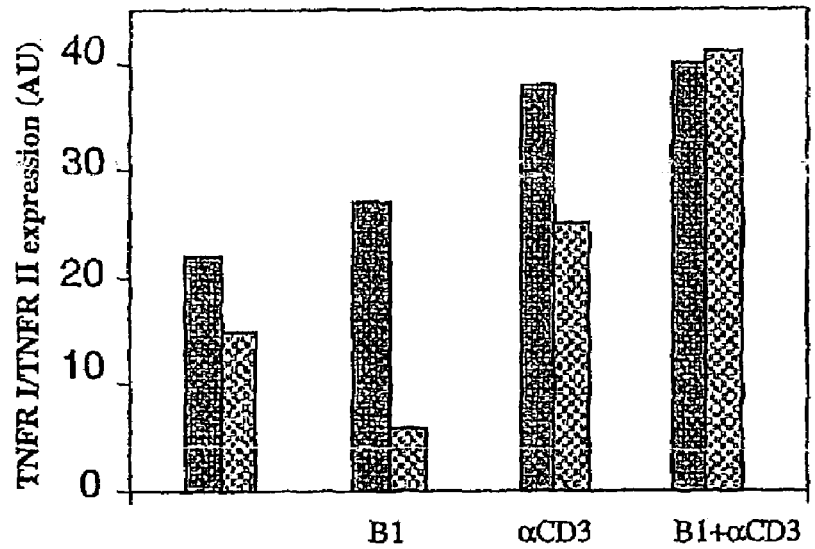
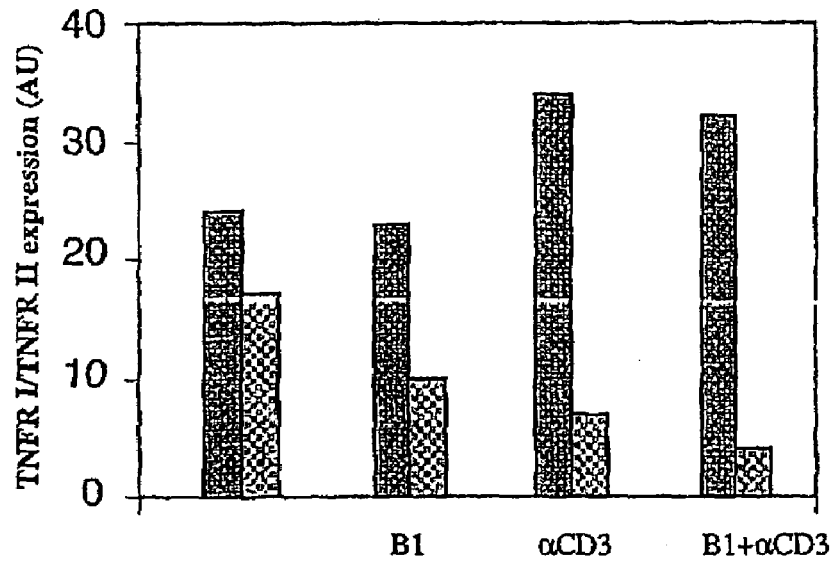

METHODS OF MODULATION OF THE IMMUNE SYSTEM

RELATED APPLICATIONS

This application is a national stage filing under 35 U.S.C. 371 of PCT application PCT/CA01/00004, filed Jan. 5, 2001, which claims priority from U.S. Provisional Application No. 60/174,710, filed Jan. 6, 2000, the specifications of each of which are incorporated by reference herein. PCT Application PCT/CA01/00004 was published under PCT Article 21(2) in English.

FIELD OF THE INVENTION

The invention relates to the field of immunology and is concerned with protein tyrosine kinases and, more particularly, to Eph-related receptor tyrosine kinases, specifically the EphB6 receptor, and its active partners, and methods of its manipulation for the modulation of cellular processes.

BACKGROUND OF THE INVENTION

The regulation of development and cell proliferation in higher organisms involves signaling through receptor tyrosine kinases (RTK). Ligand binding to the extracellular domain of RTKs induces receptor dimerization or oligomerization and stimulates their intrinsic tyrosine kinase activity (Honegger et al. (1990); Kashles et al. (1991); Ueno et al. (1991); Yarden and Schlessinger (1987); Yarden and Schlessinger (1987a)). As a consequence, RTKs undergo autophosphorylation, causing further changes in receptor configuration and providing specific docking sites for cytoplasmic signaling proteins containing Src-homology 2 (SH2) or phosphotyrosine binding (PTB) domains (Kavanaugh et al. (1995); Koch et al. (1991); Songyang et al. (1993)).

RTKs are divided into families on the basis of their structural organization (van der Geer et al. (1994)), Eph receptors forming the largest known family, with at least 14 members (Pasquale (1997); Zhou (1998); Zisch and Pasquale (1997)). Ephs bind a group of ligands known as ephrins (Eph family receptor interacting), eight of which are currently known, all membrane anchored either by glycosylphosphatidylinositol (GPI) (ephrinA1-A5), or a transmembrane domain (ephrinB1-B3) (Drescher (1997); Pasquale (1997)). Eph receptors are divided into two groups based upon their ligand binding characteristics, EphA or EphB, according to the class of ephrin bound (Brambilla et al. (1995); Ciossek and Ullrich (1997); Gale et al. (1996); Kozlosky et al. (1995); Park and Sanchez (1997)); although receptor-ligand specificity is degenerate within a group (Zhou (1998)). It is a characteristic of the Eph receptor family that their ligands must be membrane bound in order to be active (Davis et al. (1994); Sakano et al. (1996); Winslow et al. (1995)). This absolute requirement for membrane anchorage of the ligand makes the formation of cell-cell contact an obligatory event in activation of the Eph receptors. Consequently, activated receptors are concentrated in areas of cell-cell contact.

The Eph receptors and their ligands are typically most highly expressed in neural and endothelial cells (Zhou (1998)) and most descriptions of their function concern the development of the nervous system and angiogenesis (Drescher et al. (1995); Friedman et al. (1996); Hornberger et al. (1999); Gao et al. (1999); Ciossek et al. (1998); Daniel et al. (1996); O'Leary et al. (1999); Pandey et al. (1995); Adams et al. (1999); Wang. et al. (1998); Yue et al. (1999)). Upon the formation of cell-cell contact, Eph receptor signaling results in reorganization of the actin cytoskeleton and integrin activation (Becker et al. (2000); Miao et al. (2000); Zou et al. (1999); Holland et al. (1997); Huynh-Do et al. (1999)). As a result, Eph receptors generate adhesive or repulsive signals and in the neural system can guide the movement of axonal growth cones, cell migration and synapse formation (Drescher et al. (1995); Hornberger et al. (1999); Ciossek et al. (1998); Yue et al. (1999); Bohme et al. (1996); Flanagan et al. (1998); Hsueh et al. (1998); Krull et al. (1997); Monschau et al. (1997); Nakamoto et al. (1996); Mellitzer et al. (1999); Smith et al. (1997); Xu et al. (1999); Torres et al. (1998)).

The most recently identified member of the Eph family is the orphan EphB6 receptor, with a structure typical of the EphB subfamily (Gurniak et al. (1996); Matsuoka et al. (1997)). While structural analysis of EphB6 reveals conservation of the major EphB receptor autophosphorylation sites (Y638 and Y644), there are several critical alterations in the tyrosine kinase domain. These include substitution of a crucial lysine residue in the ATP binding site, resulting in a receptor that does not demonstrate detectable kinase activity (Gurniak et al. (1996); Matsuoka et al. (1997)). This casts doubt upon the ability of EphB6 to undergo tyrosine phosphorylation upon ligand stimulation and thus to initiate signaling cascades in the cytoplasm. However, analogy with ErbB-3, a well-characterized catalytically inactive member of the EGF receptor family, suggests that EphB6 may form hetero-oligiomers with catalytically active family members. And similarly, as a result of trans-phosphorylation by these active receptors, EphB6 may recruit cytoplasmic signal transducing molecules.

Unlike other receptor tyrosine kinases, EphB6 is predominantly expressed in the thymus (Gurniak et al. (1996)), suggesting that it may play an important role in T cell differentiation. Current evidence suggest that Eph receptors may directly interact with the TCR (T cell receptor) signaling pathway. Eph receptors can regulate integrin activation and cytoskeletal rearrangement (Becker et al. (2000); Miao et al. (2000); Zou et al. (1999); Holland et al. (1997); Huynh-Do et al. (1999)), both crucial events in TCR induced responses (Holsinger et al. (1998); Abraham et al. (1999); Bleijs et al. (1999); (Ticchioni et al. (1993); Valitutti et al. (1995); Wulfing et al. (1998); Wulfing et al. (1998); Snapper et al. (1998); Viola et al. (1999); Vivinus-Nebot et al. (1999)). Moreover, several Eph receptors also bind the T cell kinase Fyn (Choi et al. (1999); Ellis et al. (1996)). Indeed, high levels of EphB6 expression have been detected in a population of human peripheral T lymphocytes, but not in B cells (Shimoyama et al. (2000)). Despite its lack of kinase activity, ephrin-B1-stimulated EphB6 undergoes tyrosine phosphorylation, which is provided by a catalytically active member of the EphB subfamily. This initiates its downstream signaling. The Jun N-terminal kinase (JNK) cascade (Becker et al. (2000)) is the major pathway downstream of the Eph receptor family, and is one of the key regulators of T cell apoptosis (Sabapathy et al. (1999); Baker et al. (1998)). It is currently not clear whether the Eph receptor family or any members, including the EphB6 receptor, have a role in such apoptosis. Regulation of this aspect of the immune system continues to be desirable.

SUMMARY OF THE INVENTION

The present inventors have demonstrated that manipulation of the kinase-inactive EphB6 receptor and its active partners allows for regulation of T cell responses preferably cell signalling and T cell proliferation.

Further, the present inventors have determined that despite its lack of kinase activity, stimulated EphB6 undergoes tyrosine phosphorylation, and that modulation of EphB6 provides a method for modulating apoptosis, preferably for the induction of Activation induced Cell Death (AICD).

Accordingly, in its broad aspect the present invention provides a method of modulating the immune system of an animal comprising administering to the animal an effective amount of a substance that modulates the expression, or activity of EphB6, or its active partner thereby modulating the immune system.

In another aspect of the present invention there is provided a method of modulating of a cell comprising administering to the cell, an effective amount of a substance that modulates the expression, or activity of EphB6, or its active partner thereby modulating the apoptosis.

According to one embodiment of the methods of the invention the substances which may be used to modulate are preferably ephrin-B1, an oligomeric or monomeric soluble EphB6 receptor, a soluble EphB6 ligand, ephrin-B2, an antibody capable of binding EphB6, an antibody fragment which is agonistic or antagonistic to EphB6, a physiological or synthetic EphB6 ligand, a soluble active EphB6 partner, an antibody or fragments thereof to an EphB6 active partner, an antisense molecule to EphB6 or its active partners, or a physiological or synthetic ligand for an EphB6 active partner, more preferably the substance is Ephrin-B1 or Ephrin B2.

According to another embodiment of the present invention there is provided a method of modulating cell proliferation comprising administering to the cell an effective amount of a substance which modulates the expression or activity of an EphB6 receptor or its active partners. Preferably the substance is ephrin-B1, an oligomeric or monomeric soluble EphB6 receptor, a soluble EphB6 ligand, ephrin-B2, an antibody capable of binding EphB6, an antibody fragment which is agonistic or antagonistic to EphB6, a physiological or synthetic EphB6 ligand, a soluble active EphB6 partner, an antibody or fragments thereof to an EphB6 active partner, an antisense molecule to EphB6 or its active partners, or a physiological or synthetic ligand for an EphB6 active partner.

According to yet another embodiment of the present invention there is provided a method of modulating a T cell response in an animal comprising administering to the animal an effective amount of a substance that modulates EphB6 expression or activity or that of its partner such that the T cell response is modulated. Preferably the substance is ephrin-B1, an oligomeric or monomeric soluble EphB6 receptor, a soluble EphB6 ligand, ephrin-B2, an antibody capable of binding EphB6, an antibody fragment which is agonistic or antagonistic to EphB6, a physiological or synthetic EphB6 ligand, a soluble active EphB6 partner, an antibody or fragments thereof to an EphB6 active partner, an antisense molecule to EphB6 or its active partners, or a physiological or synthetic ligand for an EphB6 active partner, more preferably the substance is Ephrin-B1 or Ephrin B2.

According to other embodiments of the methods of the present invention a substance which stimulates EphB6 is co-administered, preferably the substance is ephrin B1, ephrin B2., or a catalytically active member of the EphB subfamily, more preferably the catalytically active member of the EphB subfamily is EphB1.

According to another embodiment of the present invention there is provided a method of treating a disorder of T-cell proliferation, an autoimmune disorder, a cell-associated autoimmune disorder, an allergic disorder in an animal, or a host versus transplant reaction comprising administering to the animal an effective amount of a combination of inhibitory or stimulatory soluble EphB6 ligand and/or soluble EphB6 receptor, or a ligand to an EphB6 active partner or soluble partner, thereby treating the disorder. Preferably the substance is ephrin-B1, an oligomeric or monomeric soluble EphB6 receptor, a soluble EphB6 ligand, ephrin-B2, an antibody capable of binding EphB6, an antibody fragment which is agonistic or antagonistic to EphB6, a physiological or synthetic EphB6 ligand, a soluble active EphB6 partner, an antibody or fragments thereof to an EphB6 active partner, an antisense molecule to EphB6 or its active partners, or a physiological or synthetic ligand for an EphB6 active partner. According to a preferred embodiment the cell-associated autoimmunity is multiple sclerosis, lupus, arthritis, thyroiditis, diabetes, psoriasis, Crohn's disease or colitis. According to another preferred embodiment of the method of the present invention, the allergic disorder is asthma, hyper-IgE syndrome, eosinophilic syndrome, or a T-cell dependent graft-verus-host disease.

According to another embodiment of the present invention there is provided a method of promoting an anti-viral immune response in an animal comprising administering to the animal an effective amount of a substance that modulates the expression or activity of EphB6 or its active Eph partner thereby promoting the antiviral response in the animal. Preferably the substance is ephrin-B1, an oligomeric or monomeric soluble EphB6 receptor, a soluble EphB6 ligand, ephrin-B2, an antibody capable of binding EphB6, an antibody fragment which is agonistic or antagonistic to EphB6, a physiological or synthetic EphB6 ligand, a soluble active EphB6 partner, an antibody or fragments thereof to an EphB6 active partner, an antisense molecule to EphB6 or its active partners, or a physiological or synthetic ligand for an EphB6 active partner, more preferably the substance is soluble stimulatory or inhibitory ephrin and/or a soluble EphB6 receptor.

According to another aspect of the methods of the present invention the animal which is subject of the methods is a mammal, preferably human.

According to another aspect of the present invention there is provided a method for identifying a substance which is capable of binding to a purified and isolated EphB6 protein, comprising reacting the protein with at least one substance which potentially can bind with the protein under conditions which permit the formation of complexes between the substance and the protein, and assaying for complexes, for free substance, for non-complexed protein, or for activation of the protein.

According to yet another aspect of the present invention there is provided a method for assaying a medium for the presence of an agonist or antagonist of the interaction of a purified and isolated a EphB6 protein and a substance which binds to the protein which comprises reacting the protein with a substance which is capable of binding to the protein and a suspected agonist or antagonist substance under conditions which permit the formation of complexes between the substance and the protein, and assaying for complexes, for free substance, for non-complexed protein, or for activation of the protein.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which:

FIG. 4A is an immunoblot illustrating pp115 co-precipitates with EphB6 in human thymocytes.

FIG. 4B is an immunoblot illustrating the time course of pp115 association with EphB6.

FIG. 4C is an immunoblot illustrating pp115 as having the same electrophoretic mobility as c-Cb1.

FIG. 4D is an immunoblot illustrating EphB6 association with Cb1 in samples immunoprecipitated from thymocyte lysates.

FIG. 4E is an immunoblot illustrating EphB6 association with Cb1 in transfected cells.

FIG. 4F is an immunoblot illustrating that the G306E loss-of-function Cb1 mutant does not bind EphB6.

FIG. 5A is an immunoblot illustrating EphB6 mediated downregulation of Zap-70.

FIG. 5B is an immunoblot illustrating that phosphorylation of Y493F Zap-70 is not altered by EphB6.

FIG. 5C is an immunoblot illustrating the stable expression of EphB6-M in transfected Jurkat.

FIG. 5D is an immunoblot illustrating the phosphorylation of EphB6-M in Jurkat with stimulation by ephrin-B1.

FIG. 5E is an immunoblot illustrating EphB6 downregulation of the phosphorylation of Zap-70.

FIG. 5F is an immunoblot illustrating EphB6 downregulation of the phosphorylation of Zap-70 associated CD3ζ in Jurkat.

FIG. 6A is an immunoblot illustrating the effect of ephrin-B1 on TCR induced activation of Lck.

FIG. 6B is an immunoblot illustrating the effect of EphB6 on TCR induced activation of Lck.

FIG. 7A provides a series of graphs illustrating the effect of ephrin-B1 on TCR mediated upregulation of CD25.

FIG. 7B provides a series of graphs illustrating the effect of overexpression of EphB6 on TCR mediated upregulation of CD25.

FIG. 8A is a histogram illustrating the enhancement of CD25 upregulation by dominant negative EphB6.

FIG. 8B is a histogram illustrating the enhancement of CD25 upregulation by dominant negative EphB6.

FIG. 9A is an immunoblot illustrating stable expression of EphB6 receptor in the mature T cell line Jurkat.

FIG. 9B is a series of figures illustrating the effect of overexpression of EphB6 upon induction of apoptosis in T-cells.

FIG. 11A is a histogram illustrating that the ephrin-B1 inhibits expression of TNFR II, but not TNFR I.

FIG. 11B is a histogram illustrating that the overexpressed EphB6 receptor inhibits expression of TNFR II, but not TNFR I.

DETAILED DESCRIPTION OF THE INVENTION

Figure 1:
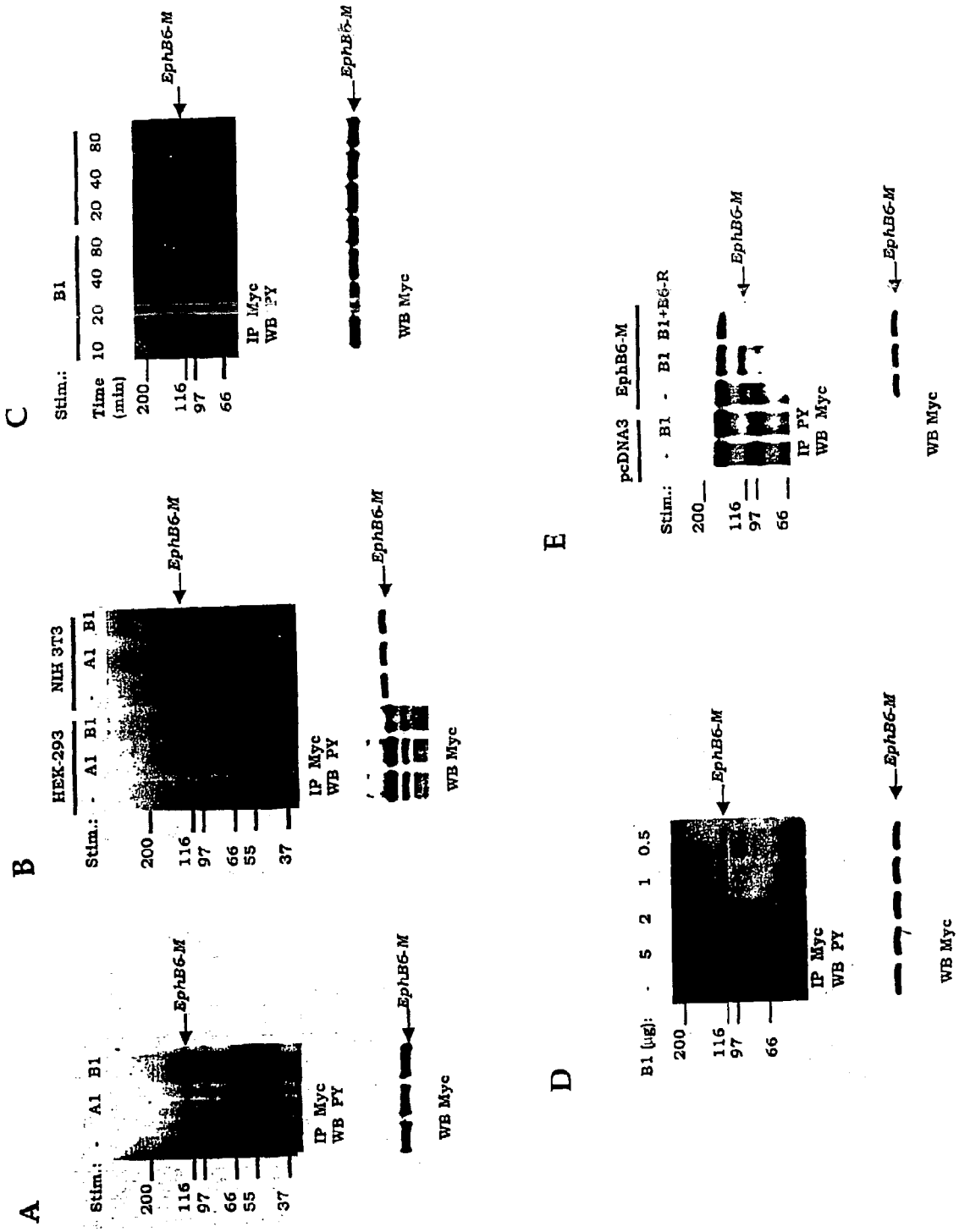
FIG. 1A is a photograph of an immunoblot illustrating EphB6-M phosphorylation in COS-7 cells upon Ephrin B1 stimulation.
FIG. 1B is a photograph of an immunoblot illustrating EphB6-M phosphorylation in Hek-295 and NIH 3T3 cells upon Ephrin B1 stimulation.
FIG. 1C is an immunoblot illustrating time dependent phosphorylation of EphB6.
FIG. 1D is an immunoblot illustrating the effects of varying ligand concentration on phosphorylation of EphB6.
FIG. 1E is an immunoblot illustrating the effect of soluble EphB6 receptor on ephrin-B1 induced EphB6 phosphorylation.

As stated above, the present inventors have demonstrated that modulation of the kinase-inactive EphB6 receptor allows for modulation of the immune system.

In particular, the inventors have determined that despite its lack of kinase activity, the EphB6 undergoes tyrosine phosphorylation upon stimulation with a substance, preferably membrane-bound or soluble oligomerized ephrin-B1. They have also demonstrated that EphB6 can be trans-phosphorylated by catalytically active members of the EphB subfamily, in particular, by EphB1.

The present inventors also demonstrate that the EphB6 receptor associates with c-Cb1, a protein central to the regulation of TCR signaling. Cb1 binding to EphB6 is constitutive, but is lost upon introduction of a Cb1 G306E 'loss of function' mutation In contrast, oncogenic 70-Z Cb1 binds EphB6 essentially like wild type Cb1.

The present inventors have also determined that, overexpression of the EphB6 receptor in T cells resulted in inhibition of anti-CD3 dependent phosphorylation of the TCR-associated kinase Zap-70 and its associated CD3ζ chain. This appeared to be mediated by a primary inhibition of the activity of the src-like kinase Lck. Ultimately, this blockage in TCR signaling results in a failure of T cell response, inhibiting upregulation of CD25 expression.

Stable overexpression of the EphB6 receptor was also found to significantly enhance TCR-mediated apoptosis in an ephrin-B1-dependent manner, thus demonstrating that modulation of EphB6 provides a method for regulating the induction of AICD.

As used herein "Behaviour of cells of the immune system" means the sum of the ability of cells to respond to a given stimulus and to interact with their environment, in particular, the rate at which they undergo proliferation, differentiation and cell death and develop immune responses.

As used herein "in conjunction with" or "co-adminstration" means concurrently, before or following adminstration of a first substance.

As used herein "animal" means any member of the animal kingdom, including, preferably, humans.

As used herein, administration of an "effective amount" of a substance or compound(s) of the present invention is defined as an amount effective, at dosages and for periods of time necessary to achieve the desired result. The effective amount of a compound of the invention may vary according to factors such as the disease state, age, sex, and weight of the animal. Dosage regima may be adjusted to provide the optimum therapeutic response. For example, several divided doses may be administered daily or the dose may be proportionally reduced as indicated by the exigencies of the therapeutic situation.

The term "active partner" as used herein means any EphB6 interacting tyrosine kinase receptor, preferably a member of the Eph family of tyrosine receptor kinases.

The EphB6 Receptor

The standard features of the EphB6 receptor place it in the EphB subfamily (Gurniak et al. (1996); Matsuoka et al. (1997)). EphB receptors are stimulated by membrane bound ephrin-B ligands demonstrating highly degenerate specificity, with ephrin-B1 and ephrin-B2 activating most EphB receptors (Zhou et al. (1998)).

Figure 3:
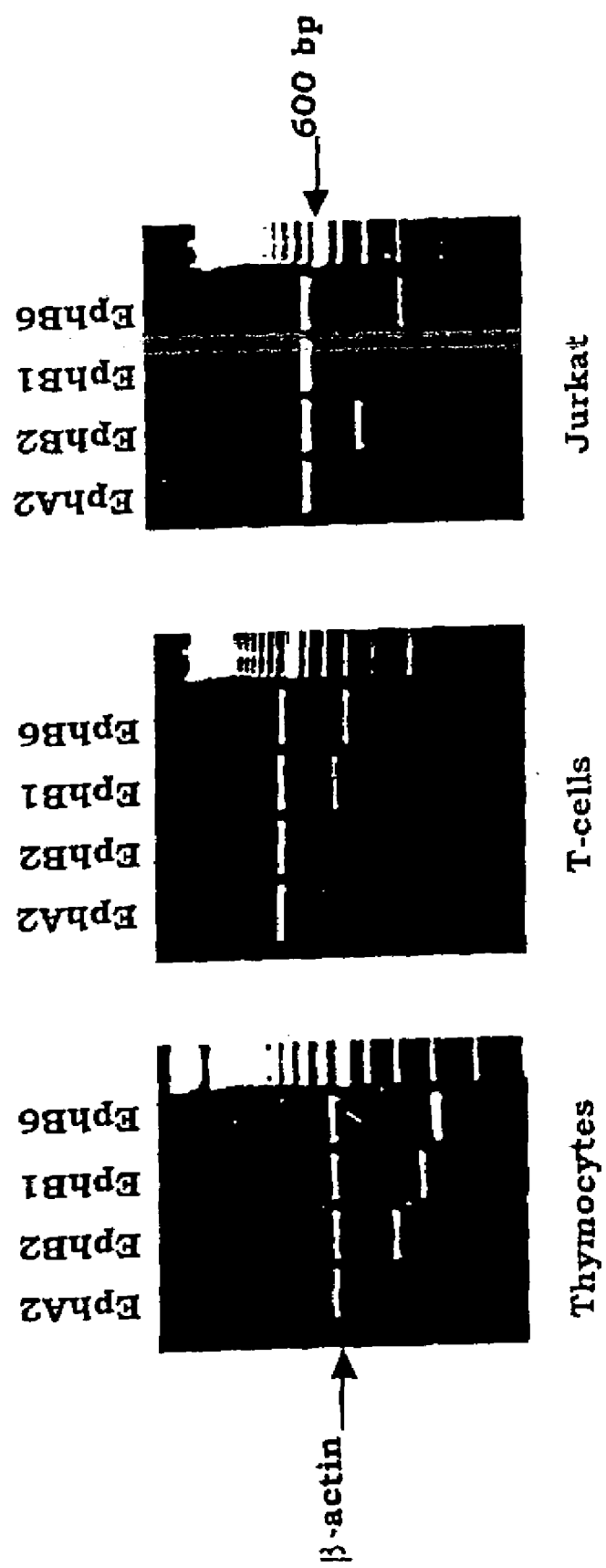
FIG. 3 is an agarose gel illustrating the expression of EpbA2, EphB1, EphB2 and EphB6 receptors in human thymocytes and T cells.

The murine EphB6 receptor was reported to be expressed predominantly in thymocytes (Gurniak et al. (1996)), suggesting that it may have an important role in T cell differentiation. By RT-PCR, the present inventors detected EphB6 expression in both human thymocytes and mature peripheral blood T cells, as well as in the T cell line Jurkat (FIG. 3). Two catalytically active members of the Eph family, EphB1 and EphB2, were also expressed throughout the T cell lineage, while the EphA2 receptor could only be detected in thymocytes. The persistent expression of EphB6 across the T cell lineage suggested it might not only be important during differentiation, but also in mature T cell function.

Due to the membrane bound nature of both the Eph receptor and ephrin ligand, an important feature of receptor-ligand interaction is the necessity for the formation of cell-cell contact. As activation of the TCR complex occurs in an area of T-cell contact with an antigen-presenting cell, activated TCR complexes may potentially be brought into close proximity with EphB receptors. TCR signaling responses are dependent upon re-organization of the actin cytoskeleton and signals transmitted via integrin receptors, both processes regulated by activated Eph receptors in a variety of cells (Holsinger et al. (1998); Abraham et al. (1999); Bleijs et al. (1999); Ticchioni et al. (1993); Valitutti et al. (1995); Wulfing and Davies (1998); Wulfing et al. (1998); Snapper et al. (1998); Viola et al. (1999); Vivinus-Nebot et al. (1999)). The potential for productive interaction between these two receptor pathways therefore appeared high.

The inventors demonstrate that activation of the T cell receptor results in association of phosphorylated carol protein with the EphB6 receptor. The ability of Cb1 to bind EphB6 suggests that analogous to the EGF receptor, EphB6 expression may be regulated by Cb1 mediated modification. It is now clear that Cb1 is responsible for the physical downregulation of many receptors through induction of receptor ubiquitination (Levkowitz et al. (1998), Wang et al. (1999), Lee et al (1999), Miyake et al. (1999). Addition of ubiquitin moieties to the lysine residues of a protein targets it for degradation (Hershko et al. (1998), either in cytoplasmic proteasomes or in lysosomes. Cb1 binding induces ubiquitination of the EGF, ErbB1, PDGF and CSF receptors, an ability derived from its ring finger domain (mutated in 70-Z Cb1). The ring-finger domain appears to be an E3 ubiquitin-ligase (Joazeiro et al. (1999)), responsible for the transfer of ubiquitin from a carrier protein (E2) to the target, thus controlling the specificity of degradation. As all receptors known to bind Cb1 undergo ubiquitination, it is likely that EphB6 function will be similarly regulated. This may provide a potential mechanism for regulating the effective cell surface expression level of the EphB6 receptor.

The inventors also demonstrate that overexpression or activation of the EphB6 receptor in T-cells can modulate signaling through the T-cell antigen receptor. Overexpression of the EphB6 receptor results in an inhibition of anti-CD3 induced activation of the Src-family kinase lck and subsequently phosphorylation of Zap-70 kinase and its associated CD3ζ chain.

Stimulation of the TCR leads in particular to induction of both IL-2 production and CD25 (IL-2Rα) expression; thus potentially inducing expansion of activated T-cell populations (Chambers et al. (1997)). TCR mediated induction of CD25 requires activation of the TCR-associated kianses. The investigators demonstrate that supression of the early events of TCR signaling by EphB6 ultimately translates into an inhibition of T-cell response, in particular, CD25 upregulation. In agreement, Ephrin-B1 stimulation of thymocytes, which naturally express high levels of EphB6, prevents TCR mediated upregulation of IL-2 receptor expression. The inhibitory effect of the endogenous EphB6 receptor upon the TCR complex was confirmed by the ability of a dominant negative form of EphB6 to enhance the TCR-induced upregulation of CD25 in T-cells. T lymphocyte homeostasis is precisely regulated, with Gus TCR co-stimulatory events required for finely tuned control of cell fate, these signals regulating both proliferative and apoptic pathways (Chambers et al. (1997), Janeway et al. (1994)). Clearly EphB6 acts as an effective TCR co-receptor, influencing the response of cells to TCR stimulation.

Expression of CD25 is central to the IL-2 driven clonal expansion that occurs upon exposure of mature T-cells to antigen. Failure to express the high affinity IL-2R complex composed of the α (CD25), β and γ chains prevents the development of the necessary IL-2 autocrine proliferative loop (Nelson and Willerford, 1998). Thus, while not wishing to be bound by any one theory, one of the biological functions of EphB6, in conjunction with other EphB receptors, may be to control the clonal expansion of antigen activated T-cells through suppression of antigen-induced CD25 expression and associated events. Several alternative models of EphB6 function also become apparent. Under physiological conditions, stimulation of the EphB6 receptor may serve to maintain activation of the TCR signaling pathway below a certain threshold, preventing premature activation by inappropriate low affinity TCR interactions. Or alternatively, the presence of varying ephrin-B ligands may modify the ability of T-cells to respond to antigens presented on different cell-surfaces. Failure to correctly regulate TCR signaling may lead to uncontrolled activation or undesirable activation upon very low affinity interaction with antigen. The consequences of these events may be multiple but include autoimmune reactions, as low affinity self-self interactions are not properly regulated, or recognition by the T-cell of inappropriate target cells due to the absence of appropriate targeting by Eph receptor engagement, or inadvertent activation of bystander cells due to cytokine overproduction by uncontrolled activated cells.

Modulation of EphB6

Antibodies

Antibodies represent a class of substances that may be used advantageously to modulate the activity of the EphB6 receptor. Antibodies may be used to either inhibit, or stimulate the EphB6 receptor. Antibodies can be prepared which bind a distinct epitope in an unconserved region of the protein. An unconsumed region of the protein is one that does not have substantial sequence homology to other proteins.

Conventional methods can be used to prepare the antibodies. For example, by using a peptide of the EphB6 receptor, polyclonal antisera or monoclonal antibodies can be made using standard methods. A mammal, (e.g., a mouse, hamster, or rabbit) can be immunized with an immunogenic form of the peptide which elicits an antibody response in the mammal. Techniques for conferring immunogenicity on a peptide include conjugation to carriers or other techniques well known in the art. For example, the protein or peptide can be administered in the presence of adjuvant. The progress of immunization can be monitored by detection of antibody titers in plasma or serum. Standard ELISA or other immunoassay procedures can be used with the immunogen as antigen to assess the levels of antibodies. Following immunization, antisera can be obtained and, if desired, polyclonal antibodies isolated from the sera.

To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art, (e.g., the hybridoma technique originally developed by Kohler and Milstein (Nature 256, 495–497 (1975)) as well as other techniques such as the human B-cell hybridoma technique (Kozbor et al., Immunol. Today 4, 72 (1983)), the EBV-hybridoma technique to produce human monoclonal antibodies (Cole et al. Monoclonal Antibodies in Cancer Therapy (1985) Allen R. Bliss, Inc., pages 77–96), and screening of combinatorial antibody libraries (Huse et al., Science 246, 1275 (1989)). Hybridoma cells can be screened immunochemically for production of antibodies specifically reactive with the peptide and the monoclonal antibodies can be isolated. Therefore, the invention also contemplates hybridoma cells secreting monoclonal antibodies with specificity for the EphB6 receptor as described herein.

The term "antibody" as used herein is intended to include fragments thereof which also specifically react with an EphB6 receptor, or peptide thereof, having the activity of the EphB6 receptor. Antibodies can be fragmented using conventional techniques and the fragments screened for utility in the same manner as described above. For example, F(ab')2 fragments can be generated by treating antibody with pepsin. The resulting F(ab')2 fragment can be treated to reduce disulfide bridges to produce Fab' fragments.

Chimeric antibody derivatives, i.e., antibody molecules that combine a non-human animal variable region and a human constant region are also contemplated within the scope of the invention. Chimeric antibody molecules can include, for example, the antigen binding domain from an antibody of a mouse, rat, or other species, with human constant regions. Conventional methods may be used to make chimeric antibodies containing the immunoglobulin variable region which recognizes the gene product of EphB6 antigens of the invention (See, for example, Morrison et al., Proc. Natl Acad. Sci. U.S.A. 81,6851 (1985); Takeda et al., Nature 314, 452 (1985), Cabilly et al., U.S. Pat. No. 4,816,567; Boss et al., U.S. Pat. No. 4,816,397; Tanaguchi et al., European Patent Publication EP171496; European Patent Publication 0173494, United Kingdom patent GB 2177096B). It is expected that chimeric antibodies would be less immunogenic in a human subject than the corresponding non-chimeric antibody.

Monoclonal or chimeric antibodies specifically reactive with a protein of the invention as described herein can be further humanized by producing human constant region chimeras, in which parts of the variable regions, particularly the conserved framework regions of the antigen-binding domain, are of human origin and only the hypervariable regions are of non-human origin. Such immunoglobulin molecules may be made by techniques known in the art, (e.g., Teng et al., Proc. Natl. Acad. Sci. U.S.A., 80, 7308–7312 (1983); Kozbor et al., Immunology Today, 4, 7279 (1983); Olsson et al., Meth. Enzymol., 92, 3–16 (1982)), and PCT Publication WO92/06193 or EP 0239400). Humanized antibodies can also be commercially produced (Scotgen Limited, 2 Holly Road, Twickenham, Middlesex, Great Britain.)

Specific antibodies, or antibody fragments, reactive against EphB6 receptor proteins may also be generated by screening expression libraries encoding immunoglobulin genes, or portions thereof, expressed in bacteria with peptides produced from the nucleic acid molecules of the EphB6 receptor. For example, complete Fab fragments, VH regions and FV regions can be expressed in bacteria using phage expression libraries (See for example Ward et al., Nature 341, 544–546: (1989); Huse et al., Science 246, 1275–1281 (1989); and McCafferty et al. Nature 348, 552–554 (1990)). Alternatively, a SCID-hu mouse, for example the model developed by Genpharm, can be used to produce antibodies or fragments thereof.

Antibodies specifically reactive with the EphB6 receptor, or derivatives thereof, such as enzyme conjugates or labeled derivatives, may be used to detect the EphB6 receptor in various biological materials, for example they may be used in any known immunoassays which rely on the binding interaction between an antigenic determinant of the EphB6 receptor, and the antibodies. Examples of such assays are radioimmunoassays, enzyme immunoassays (e.g. ELISA), immunoflurorescence, immunoprecipitation, latex agglutination, hemagglutination and histochemical tests. Thus, the antibodies may be used to detect and quantify the EphB6 receptor in a sample in order to determine its role in particular cellular events or pathological states, and to diagnose and treat such pathological states.

In particular, the antibodies of the invention may be used in immuno-histochemical analyses, for example, at the cellular and sub-subcellular level, to detect the EphB6 receptor, to localise it to particular cells and tissues and to specific subcellular locations, and to quantitate the level of expression.

Cytochemical techniques known in the art for localizing antigens using light and electron microscopy may be used to detect the EphB6 receptor. Generally, an antibody of the invention may be labelled with a detectable substance and the EphB6 receptor may be localised in tissue based upon the presence of the detectable substance. Examples of detectable substances include various enzymes, fluorescent materials, luminescent materials and radioactive materials. Examples of suitable enzymes include horseradish peroxidase, biotin, alkaline phosphatase, β-galactosidase, or acetylcholinesterase; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include radioactive iodine I-125, I-131 or 3-H. Antibodies may also be coupled to electron dense substances, such as ferritin or colloidal gold, which are readily visualised by electron microscopy.

Indirect methods may also be employed in which the primary antigen-antibody reaction is amplified by the introduction of a second antibody, having specificity for the antibody reactive against the EphB6 receptor. By way of example, if the antibody having specificity against the EphB6 receptor is a rabbit IgG antibody, the second antibody may be goat anti-rabbit gamma-globulin labelled with a detectable substance as described herein.

Where a radioactive label is used as a detectable substance, the EphB6 receptor may be localized by autoradiography. The results of autoradiography may be quantitated by determining the density of particles in the autoradiographs by various optical methods, or by counting the grains.

Soluble proteins represent another class of substances that may be used advantageously to modulate the activity of the EphB6 receptor. Soluble proteins can be prepared by a number of conventional methodologies. GST fusion proteins of Eph receptor and ephrin extracellular domains, or activated or inactive variants thereof, can be created in the pGEX vector series (Pharmacia Biotech, Uppsala). When the vectors containing the cDNAs are transformed into bacteria by heat shock uptake, expression of the GSI fusion proteins can be induced with 1 mM IPTG. After growth bacteria can be lysed by sonication and the addition of mild detergents. the resulting supernatant can be clarified by centrifugation and the released GST-fusion proteins purified by binding to glutathione-sepharose. After extensive washing these complexes can be checked for purity and quantitated by reference to standard proteins of similar molecular weight after staining with coomassie blue. Alternatively fusions of the Eph or ephrin proteins with MBP, His, thioHis, Fc, Myc tag, HA tag, or other epitopes or domains may be used to allow other purification procedures to be utilized which may result in preferable activity of the purified protein.

It would also be apparent to one skilled in the art that the above described methods may be used to study the expression of the EphB6 receptor and, accordingly, will provide further insight into the role of the EphB6 receptor in cells.

Antisense Oligonucleotides

Antisense oligonucleotides that are complimentary to a nucleic acid sequence from the EphB6 receptor can also be used in the methods of the present invention to modulate the expression and/or activity EphB6 receptors.

Accordingly, the present invention provides a method of modulating the immune system by modulating the expression and/or activity EphB6 receptors comprising administering an effective amount of an antisense oligonucleotide that is complimentary to a nucleic acid sequence from the EphB6 receptor to an animal in need thereof.

The term "antisense oligonucleotide" as used herein means a nucleotide sequence that is complimentary to its target.

The term "oligonucleotide" refers to an oligomer or polymer of nucleotide or nucleoside monomers consisting of naturally occurring bases, sugars, and intersugar (backbone) linkages. The term also includes modified or substituted oligomers comprising non-naturally occurring monomers or portions thereof, which function similarly. Such modified or substituted oligonucleotides may be preferred over naturally occurring forms because of properties such as enhanced cellular uptake, or increased stability in the presence of nucleases. The term also includes chimeric oligonucleotides which contain two or more chemically distinct regions. For example, chimeric oligonucleotides may contain at least one region of modified nucleotides that confer beneficial properties (e.g. increased nuclease resistance, increased uptake into cells), or two or more oligonucleotides of the invention may be joined to form a chimeric oligonucleotide.

The antisense oligonucleotides of the present invention may be ribonucleic or deoxyribonucleic acids and may contain naturally occurring bases including adenine, guanine, cytosine, thymidine and uracil. The oligonucleotides may also contain modified bases such as xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thiolalkyl guanines, 8-hydroxyl guanine and other 8-substituted guanines, other aza and deaza uracils, thymidines, cytosines, adenines, or guanines, 5-trifluoromethyl uracil and 5-trifluoro cytosine.

Other antisense oligonucleotides of the invention may contain modified phosphorous, oxygen heteroatoms in the phosphate backbone, short chain alkyl or cycloalkyl intersugar linkages or short chain heteroatomic or heterocyclic intersugar linkages. For example, the antisense oligonucleotides may contain phosphorothioates, phosphotriesters, methyl phosphonates, and phosphorodithioates. In an embodiment of the invention there are phosphorothioate bonds links between the four to six 3'-terminus bases. In another embodiment phosphorothioate bonds link all the nucleotides.

The antisense oligonucleotides of the invention may also comprise nucleotide analogs that may be better suited as therapeutic or experimental reagents. An example of an oligonucleotide analogue is a peptide nucleic acid (PNA) wherein the deoxyribose (or ribose) phosphate backbone in the DNA (or RNA), is replaced with a polyamide backbone which is similar to that found in peptides (P. E. Nielsen, et al Science 1991, 254, 1497). PNA analogues have been shown to be resistant to degradation by enzymes and to have extended lives in vivo and in vitro. PNAs also bind stronger to a complimentary DNA sequence due to the lack of charge repulsion between the PNA strand and the DNA strand. Other oligonucleotides may contain nucleotides containing polymer backbones, cyclic backbones, or acyclic backbones. For example, the nucleotides may have morpholino backbone structures (U.S. Pat. No. 5,034,506). Oligonucleotides may also contain groups such as reporter groups, a group for improving the pharmacokinetic properties of an oligonucleotide, or a group for improving the pharmacodynamic properties of an antisense oligonucleotide. Antisense oligonucleotides may also have sugar mimetics.

The antisense nucleic acid molecules may be constructed using chemical synthesis and enzymatic ligation reactions using procedures known in the art. The antisense nucleic acid molecules of the invention or a fragment thereof, may be chemically synthesized using naturally occurring nucleotides or variously modified nucleotides designed to increase the biological stability of the molecules or to increase the physical stability of the duplex formed with mRNA or the native gene e.g. phosphorothioate derivatives and acridine substituted nucleotides. The antisense sequences may be produced biologically using an expression vector introduced into cells in the form of a recombinant plasmid, phagemid or attenuated virus in which antisense sequences are produced under the control of a high efficiency regulatory region, the activity of which may be determined by the cell type into which the vector is introduced.

The antisense oligonucleotides may be introduced into tissues or cells using techniques in the art including vectors (retroviral vectors, adenoviral vectors and DNA virus vectors) or physical techniques such as microinjection. The antisense oligonucleotides may be directly administered in vivo or may be used to transfect cells in vitro which are then administered in vivo. In one embodiment, the antisense oligonucleotide may be delivered to macrophages and/or endothelial cells in a liposome formulation.

Modulation of EphB6 Promoter

As would be readily apparent to those skilled in the art, it is also possible to modulate EphB6 through manipulation of its promoter. One or more alterations to a promoter sequence of the EphB6 may increase or decrease promoter activity, or increase or decrease the magnitude of the effect of a substance able to modulate the promoter activity.

"Promoter activity" is used to refer to the ability to initiate transcription. The level of promoter activity is quantifiable for instance by assessment of the amount of mRNA produced by transcription from the promoter or by assessment of the amount of protein product produced by translation of mRNA produced by transcription from the promoter. The amount of a specific mRNA present in an expression system may be determined for example using specific oligonucleotides which are able to hybridise with the mRNA and which are labelled or may be used in a specific amplification reaction such as the polymerase chain reaction.

Substances which affect the EphB6 promoter's activity may also be identified using the methods of the invention by comparing the pattern and level of expression of a reporter gene, in cells in the presence, and in the absence of the substance. Accordingly a method for assaying for the presence of an agonist or antagonist of EphB6 promoter activity is provided comprising providing a cell containing a reporter gene under the control of the promoter with a substance which is a suspected agonist or antagonist under conditions which permit interaction and assaying for the increase or decrease of reporter gene product.

Apoptosis of Cells

Activation induced apoptosis (programmed cell death) maintains homeostasis and immune tolerance by regulating the number and type of antigen stimulated T-cells in circulation. Activation induced cell death (ACID) can be provoked in antigen-stimulated T-cells to eliminate potentially harmful cells and excessive clonotypes, thus preserving the functional balance of the immune system, preventing autoimmune and lympho-proliferative disorders (Park et al. (1997); Davis et al. (1994); Sakano et al. (1996)).

The investigators demonstrate that stable overexpression of the EphB6 receptor significantly enhances TCR-mediated apoptosis in an ephrin-B1-dependent manner in the mature T-cell line Jurkat; a commonly used model of pre-stimulated mature T cells in ACID studies. Active T-cell apoptosis is driven by the antigen-induced expression of the FASL and TNF death cytoidnes (Friedman et al. (1996); Hornberger et al. (1999); Gao et al. (1999); Ciossek et al. (1998)). The increased apoptosis observed in EphB6 overexpressing cells appears to be due in part to increased TNP production. Although TNF efficiently activates both the TNFR-I and TNFR-II receptors, studies suggest that only TNFR-I is coupled to a caspase cascade (Kozlosky et al. (1995)) and thus may be the predominant transmitter of the apoptic signal (Daniel et al. (1996); O'Leary et al. (1999)). Expression of TNFR-II, but not TNFR-I, is suppressed upon incubation of control and EphB6 overexpressing cells with ephrin-B1. Although activation of the TCR overrides this effect in control cells, overexpression of EphB6 maintains the ephrin-B1-induced down regulation of TNFR-II. Anti-CD3 stimulation of EphB6 overexpressing cells also reduces TNFR-II expression, while it has no effect upon the receptor in control cells, suggesting that the basal activity of overexpressed EphB6 receptor is sufficient to make cells more sensitive to the induction of apoptosis. The EphB6-induced imbalance in TNFR-I and TNFR-II expression is interestingly similar to the situation observed in the T-cells of aging humans, where TNFR-I is constitutively expressed and TNFR-II is downregulated. These T-cells are hypersensitive to TNF-induced apoptosis, which is probably responsible for increasing T-cell deficiency in old-age (Pandey et al. (1995)). Eph receptors could potentially be responsible for this alteration in TNP receptor expression and modulation of their activity could improve TNFR-II expression.

TNFR-I and TNFR-II employ only partially distinct signaling pathways, both initiating the n-terminal JUN kinase cascade (Kozlosky et al. (1995)). Activation of the JNK pathway is required to protect cells from TNF-mediated apoptosis (Adams et al. (1999), Wang et al. (1998)). Overexpression of EphB6 strongly inhibits long-term anti-CD3 induced JNK stimulation. This effect is highly specific, several other potentially anti-apoptic pathways, including Akt activation and Bcl-2 expression, are not affected. The elimination of JNK-JUN signaling reportedly enhances TNF-induced apoptosis (Adams et al. (1999); Wang et al. (1998)), suggesting that selective inhibition of the JUN kinase pathway could further the promotion of AICD by EphB6.

Thus, and while not wishing to be bound by any particular theory, the increase in inducible programmed cell death in EphB6 overexpressing cells can be attributed at least in part to increased TNF production, complemented by an alteration in the balance between TNFR-I and TNFR-II expression to favor the pro-apoptic TNFR-I. Accordingly, the present invention provides a method of regulating the immune system, preferably regulating lymphocyte apoptosis, preferably AICD, by providing an effective amount of a substance capable of modulation of EphB6 and its active partners, thereby modulating the immune system.

The high level of EphB6 expression in thymocytes also suggests that EphB6 may play an important role in vivo in the negative and positive selection of thymocytes, regulating the induction of the apoptic pathway in cells that fail to be positively selected. Failure to properly regulate negative selection can lead to the emergence of auto-reactive T-cells in the periphery leading to the development of autoimmune diseases. In the peripheral blood, failure to eliminate activated T-cells may result in T-cell lymphoproliferative disorders or auto-immune disorders as the result of an inability to eliminate self reactive T-cells.

Therapeutic Uses

As just discussed, the EphB6 receptor of the invention is likely involved in the regulation of cell signalling pathways that control cell death. Accordingly, the present invention provides a method of modulating cell death or apoptosis comprising administering to a cell or animal in need thereof, an effective amount of a substance that modulates EphB6, in order to modulate the cell death. Examples of substance which may be used to modulate EphB6 include antibodies, soluble EphB6, soluble ephrins, antisense nucleic acids, organic substances that modulate the interaction of EphB6 with ligands and active partners either alone or in combination. The term "effective amount" as used herein means an amount effective, at dosages and for periods of time necessary to achieve the desired results.

In another aspect the present invention provides a method of modulation of cell proliferation. In one embodiment, the invention provides a method of inhibiting or reducing cell proliferation, such as in neoplasia, by administering to a cell or animal an effective amount of an agent that promotes the expression or the biological activity of the EphB6 receptor or its active Eph partners, such that there is an inhibition or reduction in cell proliferation.

In another embodiment, the present invention provides a method of inducing cell proliferation by administering to a cell or an animal an effective amount of a substance that inhibits the expression or the biological activity of the EphB6 receptor, or blocks the phosphorylation of the said receptor or its active Eph partners, such that there is an induction of cell proliferation. Substances that inhibit the activity of the EphB6 receptor include antibodies to EphB6 receptor. Substances that inhibit the expression of the EphB6 gene include antisense oligonucleotides to an EphB6 receptor nucleic acid sequence.

In addition to antibodies and antisense oligonucleotides, other substances that modulate EphB6 receptor expression or activity may also be identified, as well as substances that block the phosphorylation of EphB6. Substances that affect EphB6 receptor activity can be identified based on their ability to bind to the EphB6 receptor.

Substances which can bind with the EphB6 receptor of the invention may be identified by reacting the EphB6 receptor with a substance which potentially binds to the EphB6 receptor, and assaying for complexes, for free substance, or for non-complexed EphB6 receptor, or for activation of the EphB6 receptor. In particular, a yeast two hybrid assay system may be used to identify proteins which interact with the EphB6 receptor (Fields, S. and Song, O., 1989, Nature, 340:245–247) or a ligand binding or ligand replacement assay system (Blechman, J. M. et al. (1993); Blechman, J. M et al. (1995); Lev et al. (1993)). Systems of analysis which also may be used include ELISA, BIAcore(Bartley, T. D., et al. (1994)).

A protein ligand for the Eph receptors can be isolated by using the extracellular domain of the receptor as an affinity reagent. Concentrated cell culture supernatants can be screened for receptor binding activity using immobilized receptor in a surface plasmon resonance detection system (BIAcore). Supernatants from selected cell lines can then be fractionated directly by receptor affinity chromatography.

Conditions which permit the formation of substance and EphB6 receptor complexes may be selected having regard to factors such as the nature and amounts of the substance and the protein.

The substance-protein complex, free substance or non-complexed proteins may be isolated by conventional isolation techniques, for example, salting out, chromatography, electrophoresis, gel filtration, fractionation, absorption, polyacrylamide gel electrophoresis, agglutination, or combinations thereof. To facilitate the assay of the components, antibody against the EphB6 receptor or the substance, or labelled EphB6 receptor, or a labelled substance may be utilized. The antibodies, proteins, or substances may be labelled with a detectable substance as described above.

Substances which bind to and activate the EphB6 receptor of the invention may be identified by assaying for phosphorylation of the tyrosine residues of the protein.

Substances which bind to and inactivate the EphB6 receptor of the invention may be identified by assaying for reduction in phosphorylation of the protein.

The EphB6 receptor, or the substance used in the method of the invention may be insolubilized. For example, the EphB6 receptor or substance may be bound to a suitable carrier. Examples of suitable carriers are agarose, cellulose, dextran, Sephadex, Sepharose, carboxymethyl cellulose polystyrene, filter paper, ion-exchange resin, plastic film, plastic tube, glass beads, polyamine-methyl vinyl-ether-maleic acid copolymer, amino acid copolymer, ethylene-maleic acid copolymer, nylon, silk, etc. The carrier may be in the shape of, for example, a tube, test plate, beads, disc, sphere etc.

The insolubilized protein or substance may be prepared by reacting the material with a suitable insoluble carrier using known chemical or physical methods, for example, cyanogen bromide coupling.

The proteins or substance may also be expressed on the surface of a cell using the methods described herein.

The invention also contemplates a method for assaying for an agonist or antagonist of the EphB6 receptor. The agonist or antagonist may be an endogenous physiological substance or it may be a natural or synthetic substance. Substances that are capable of binding the EphB6 receptor may be identified using the methods set forth herein.

The invention also contemplates assaying for an antagonist or agonist of the EphB receptor and its active partner or partners preferably an Eph receptor.

It will be understood that the agonists and antagonists that can be assayed using the methods of the invention may act an one or more of the binding sites an the protein or substance including agonist binding sites, competitive antagonist binding sites, non-competitive antagonist binding sites or allosteric sites.

The invention also makes it possible to screen for antagonists that inhibit the effects of an agonist of the EphB6 receptor or its active partners. Thus, the invention may be used to assay for a substance that competes for the same binding site of the EphB6 receptor or its active partners.

The methods described above may be used to identify a substance which is capable of binding to an activated EphB6 receptor or its active partners, and to assay for an agonist or antagonist of the binding of activated EphB6 receptor or its partners, with a substance which is capable of binding with activated EphB6 receptor or its partners. An activated (i.e. phosphorylated) the EphB6 receptor may be prepared using the methods described (for example in Reedijk et al. The EMBO Journal, 11(4):1365, 1992) for producing a tyrosine phosphorylated protein.

It will also be appreciated that intracellular substances which are capable of binding to EphB6 or its active partners may be identified using the methods described herein.

The invention further provides a method for assaying for a substance that affects an EphB6 receptor regulatory pathway comprising administering to a human or animal or to a cell, or a tissue of an animal, a substance suspected of affecting a EphB6 receptor regulatory pathway, and quantitating the EphB6 receptor or nucleic acids encoding the EphB6 receptor, or examining the pattern and/or level of expression of EphB6 receptor, in the human or animal or tissue, or cell. EphB6 receptor may be quantitated and its expression may be examined using. the methods described herein.

The substances identified by the methods described herein, may be used for modulating EphB6 receptor regulatory pathways and accordingly may be used in the treatment of conditions involving perturbation of EphB6 receptor signaling pathways. In particular, the substances may be particularly useful in the treatment of disorders of cell death.

As stated previously, EphB6 receptor may be involved in modulating cell proliferation and stimulators and inhibitors of the EphB6 receptor may be useful in modulating disorders involving cell proliferation such as neoplasia and autoimmunity, such as for example, substances that stimulate the EphB6 receptor (for example, identified using the methods of the invention) may be used to stimulate cell death or apoptosis, and inhibitors could be used where an increase in T cell proliferation would be advantageous.

Peptide Mimetics

The present invention also includes peptide mimetics of the EphB6 receptor of the invention. For example, a peptide derived from a binding domain of an EphB6 protein will interact directly or indirectly with an associated molecule in such a way as to mimic the native binding domain. Such peptides may include competitive inhibitors, enhancers, peptide mimetics, and the like. All of these peptides as well as molecules substantially homologous, complementary or otherwise functionally or structurally equivalent to these peptides may be used for purposes of the present invention.

"Peptide mimetics" are structures which serve as substitutes for peptides in interactions between molecules (See Morgan et al (1989), Ann. Reports Med. Chem. 24:243–252 for a review). Peptide mimetics include synthetic structures which may or may not contain amino acids and/or peptide bonds but retain the structural and functional features of a peptide, or enhancer or inhibitor of the invention. Peptide mimetics also include peptoids, oligopeptoids (Simon et al (1972) Proc. Natl. Acad, Sci USA 89:9367); and peptide libraries containing peptides of a designed length representing all possible sequences of amino acids corresponding to a peptide of the invention.

Peptide mimetics may be designed based on information obtained by systematic replacement of L-amino acids by D-amino acids, replacement of side chains with groups having different electronic properties, and by systematic replacement of peptide bonds with amide bond replacements. Local conformational constraints can also be introduced to determine conformational requirements for activity of a candidate peptide mimetic. The mimetics may include isosteric amide bonds, or D-amino acids to stabilize or promote reverse turn conformations and to help stabilize the molecule. Cyclic amino add analogues may be used to constrain amino add residues to particular conformational states. The mimetics can also include mimics of inhibitor peptide secondary structures. These structures can model the 3-dimensional orientation of amino acid residues into the known secondary conformations of proteins. Peptoids may also be used which are oligomers of N-substituted amino acids and can be used as motifs for the generation of chemically diverse libraries of novel molecules.

Peptides of the invention may also be used to identify lead sounds for drug development. The structure of the peptides described herein can be readily determined by a number of methods such as NMR and X-ray crystallography. A comparison of the structures of peptides similar in sequence, but differing in the biological activities they elicit in target molecules can provide information about the structure-activity relationship of the target. Information obtained from the examination of structure-activity relationships can be used to design either modified peptides, or other small molecules or lead compounds which can be tested for predicted properties as related to the target molecule. The activity of the lead compounds can be evaluated using assays similar to those described herein.

Information about structure-activity relationships may also be obtained from co-crystallization studies. In these studies, a peptide with a desired activity is crystallized in association with a target molecule, and the X-ray structure of the complex is determined. The structure can then be compared to the structure of the target molecule in its native state, and information from such a comparison maybe used to design compounds expected to possess.

The invention also makes it possible to screen for antagonists that inhibit the effects of an EphB6 receptor. Thus, the invention may be used to assay for a substance that anatagonizes or blocks the action of the receptor.

The invention further provides a method for assaying for a substance that affects the EphB6 receptor, comprising administering to a non-human animal or to a tissue of an animal, a substance suspected of affecting the activity or action of the receptor and quantitating the effect an CD25 expression in the human animal or tissue. CD25 may be quantitated and its expression may be examined using the methods described herein.

Substances identified by the methods described herein, may be used for modulating EphB6 receptor activity or action and accordingly may be used in the treatment of conditions involving perturbation of the protein. In particular, the substances may be particularly useful in the treatment of disorders of T-cell proliferation. In addition, the application of a proper combination of inhibitory or stimulatory soluble ligand or soluble receptors should prevent T lymphocyte-target cell interaction and decrease host reaction versus transplant, thus inhibiting transplant rejection. As well, by virtue of the methods and substances of the present invention, the employment of inhibitory or stimulatory soluble ligands and soluble receptors may be used for treatment or slowing of autoimmune disorders. Such autoimmune disorders may include cell-associated autoimmunities such as multiple sclerosis, lupus, arthritis, thyroiditis, diabetes, psoriasis and Crohn's disease and colitis. In addition, the methods and substances may be used to treat allergic disorders such as asthma and hyper-IgE and eosinophilic syndromes and T-cell dependent graft-verus-host reactions. As well, by virtue of the substances and methods described herein, soluble stimulatory or inhibitory ephrins and soluble receptors could promote both T lymphocyte adhesion and T cell response to infected cells, thus accelerating and increasing anti-viral immune response.

It is also envisaged that the DNA sequences of the EphB6 receptor or its active partners might be determined in order to assay for changes, preferably disease-causing mutations that may be used as indicators of disease prognosis or as aids to inform treatment of these diseases.

Pharmaceutical Compositions

The above described substances may be formulated into pharmaceutical compositions for adminstration to subjects in a biologically compatible form suitable for administration in vivo. By "biologically compatible form suitable for administration in vivo" is meant a form of the substance to be administered in which any toxic effects are outweighed by the therapeutic effects. The substances may be administered to living organisms including humans, and animals.

Administration of a therapeutically active amount of pharmaceutical compositions of the present invention is defined as an amount effective, at dosages and for periods of time necessary to achieve the desired result. For example, a therapeutically active amount of a substance may vary according to factors such as the disease state, age, sex, and weight of the individual, and the ability of the substance to elicit a desired response in the individual. Dosage regima may be adjusted to provide the optimum therapeutic response. For example, several divided doses may be administered daily or the dose may be proportionally reduced as indicated by the exigencies of the therapeutic situation.

An active substance may be administered in a convenient manner such as by injection (subcutaneous, intravenous, etc.), oral administration, inhalation, transdermal application, or rectal administration. Depending an the route of administration, the active substance may be coated in a material to protect the compound from the action of enzymes, acids and other natural conditions which may inactivate the compound. If the active substance is a nucleic acid encoding, for example, a modified EphB6 receptor it may be delivered using techniques known in the art.

The compositions described herein can be prepared by per se known methods for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985) or Handbook of Pharmaceutical Additives (compiled by Michael and Irene Ash, Gower Publishing Limited, Aldershot, England (1995)). On this basis, the compositions include, albeit not exclusively, solutions of the substances in association with one or more pharmaceutically acceptable vehicles or diluents, and may be contained in buffered solutions with a suitable pH and/or be iso-osmotic with physiological fluids. In this regard, reference can be made to U.S. Pat. No. 5,843,456. As will also be appreciated by those skilled, administration of substances described herein may be by an inactive viral carrier.

Experimental Models

The invention also provides methods for studying the function of EphB6 and its impact on cells of the immune system.

The following non-limiting examples are illustrative of the present invention:

EXAMPLES

General Methods for Examples 1–5

Antibodies and Recombinant Proteins.

Monoclonal anti-phosphotyrosine was obtained from Upstate Biotechnology, Inc. (Lake Placid, N.Y.). Antibodies to EphB6, MYC, Zap-70 and LCK were purchased from Santa Cruz Biotechnology, Inc. (Santa Cruz, Calif.). Soluble dimerized Ephrin-B1 and soluble EphB6 receptors were purchased from R&D Systems. Anti-human CD3 was purchased from Serotec (UK) and anti-T7 from Novagen.

Immunoprecipitation and Western Blotting

Cells were quickly resuspended in ice cold lysis buffer consisting of 50 mM Tris-HCl pH 7.5, 150 mM NaCl, 10% glycerol, 1% Triton X-100, 1 mM ethylene glycol-bis (β-aminoethylether)-N,N,N'-N'-tetraacetic acid (EGTA), 10 µg/ml leupeptin, 10 µg/ml aprotinin, 1 mm PMSF, 1 mM Na-orthovanadate and 50 mM NaF after solubilization on ice for 15 minutes, debris was removed by centrifugation at 12,000 g for 10 minutes at 4° C. antibodies and 20 µl of 50% protein G sepharose were added to cleared lysates and incubated at 4° C. with constant shaking for 12–16 hours. Immunoprecipitates were collected by a brief centrifugation and washed 3–4 times in lysis buffer (without PMSF) before addition of SDS sample buffer. Samples were separated on SDS-polyacrylamide gels and transferred to nitrocellulose membranes (Amersham, Arlington Heights, Ill.). Membranes were blocked overnight at 4° C. with 7% blotting grade non-fat milk (Biorad, Richmond, Calif.) in PBS. Immunoblotting antibodies were added at optimal dilutions in PB-ST (0.1% Tween-20) and incubated at 4° C. overnight. After extensive washing with PBS-T, bound antibodies were detected using horseradish-peroxidase conjugated donkey anti-rabbit or sheep anti-mouse antibodies (Amersham, Arlington Heights, Ill.) and lumiglo chemiluminescent reagents (Kirkegaard and Perry, Mass.).

Kinase Assays.

Kinase immunoprecipitates were prepared as above in 1% Triton X-100 lysis buffer, given one wash in kinase buffer before incubation in 50 µl of kinase buffer (20 mM HEPES pH 7.6, 10 mM $MgCl_2$) in the presence of 4 µg of the synthetic substrate peptide raytide EL (Oncogene) and $\gamma[^{33}p]$-ATP for 15 min at room temperature. The kinase buffer containing the labeled peptide was collected and loaded onto phosphocellulose paper discs. The paper was washed 3 times with 0.5% phosphoric acid to remove unincorporated $^{33}P$-ATP and once with acetone, dried and counted in a β-counter. Results are shown in arbitrary units and each represents one of four independent experiments. The presence of Lck was determined by immunoblotting lck immunoprecipitates run on non-reducing SDS page with anti-Lck (not shown).

Subcloning and Mutation of Zap-70, Cb1, EphB6 and EphB1 cDNAs for Zap-70, Cb1, EphB1, EphB6, ephrin-A1 and ephrin-B1 were cloned from normal human thymocyte RNA by RT-PCR into the expression vector pcDNA3 (Invitrogen, CA) and sequenced. Mutants of these molecules (Zap: Y493F, Cb1 G306E, 70-Z) (EphB1: truncation of 102 C-terminal amino acids, knase-null K651Q) (EphB6-DN: deletion of cytoplasmic tail) were created using the overlapping PCR technique to introduce the required base changes, using cloned cDNAs as the template. Kinase-null B1 was created by mutating lysine 651 to glutamine (K651Q). The resulting cDNAs were cloned and sequenced to confirm the mutations. Myc-tagged versions of EphB6 and of the truncated EphB1 receptor were generated by insertion of a Myc tag and constructs verified by sequencing. Expression of wild type proteins and mutants were examined by transfection in COS-7 cells and western blotting with appropriate antibodies. All mutations were expressed as well as respective wild types. The truncated form of EphB1 was an active kinase, like the wild type protein. Kinase-null EphB1 had no detectable kinase activity.

Transfection of Cell Lines.

Adherent COS-7, HEK 293 and NIH 3T3 cells were routinely transiently transfected using the lipid reagent lipofectamine (Life Technologies, Grand Island, N.Y.). The DNA-lipid mixtures were applied to the cells for 5 hours in the absence of serum, before the addition of complete medium. Cells were given 72 hours to express the transfected proteins before harvest.

To raise stable EphB6 overexpressing cells, the mature human T-cell line jurkat was transfected with empty pcDNA3, EphB6-M, or DN-BphB6. The jurkat cells were electroporated in 400 µl complete RPMI medium with 30 µg of DNA by pulsing once for 65 msec at 260V (BTK electro square porator, BTX, division of Genetronics Inc, San Diego, Calif.). Cells were incubated at 37° C. for 24 hours before addition of G418 to the medium. After 30 days of selection the resulting oligoclonal cell populations were screened by immunoprecipitation with anti-MYC and western blotting with anti-myc or anti-EphB6 and the highest EphB6 expressing cell population (B6-J) selected.

Isolation of Human Thymocytes.

Thymuses were obtained from children undergoing open heart surgery. Mononuclear cells were isolated by Ficoll-hypaque gradient centrifugation. Adherent cells were removed by incubation to plastic dishes for 60 minutes at 37° C. The resulting thymocytes are typically >95% CD3.

Stimulation of EphB6 Receptor Transfected Cells with Membrane Bound and Soluble Ligand.

To assay for stimulation with membrane bound forms of the ephrin ligands, receptor-expressing cells were resuspended using 2.5 mM EDTA and after washing, overlaid on a confluent monolayer of control or ligand-expressing cells. After incubation at 37° C. for 1 hour, all the cells were solubilized in 1% Triton lysis buffer. Soluble ephrin-B1-Fc fusion-protein dimer was purchased from R&D Systems (Minneapolis, Minn.). The dimeric ephrin-B1 fusion protein was pre-complexed with $F(ab)'_2$ goat anti-human Fc (pierce) to form oligomers. $F(ab)'_2$ goat anti-human Fc was used as a control (no stimulation) where necessary. Although murine ephrin-B1 was utilized, this effectively induced human EphB6 phosphorylation.

Analysis of CD25 Expression by Flow Cytometry.

Cells were incubated in 0.5% serum for 24 hours with or without 5 µg/ml soluble oligomerized or immobilized ephrin-B1 and immobilized anti-CD3 antibody. Anti-human-CD19 antibody was used as an irrelevant protein control for immobilized ephrin-B1 where necesssary. The expression of CD25 was then analyzed by staining with pre-labeled anti-CD25 and isotype control Immunotech).

Example 1

To determine if the catalytically inactive EphB6 receptor could be tyrosine phosphorylated in response to ephrin-B ligand stimulation, we transiently expressed human EphB6 in COS-7 cells and exposed those cells to ephrin-B1. The EphB6 receptor was expressed as a C-terminal myc-tagged protein (EphB6-M). To provide cell surface expressed ligands, we transfected COS-7 cells with pcDNA3 expression vector containing either ephrin-A1 or ephrin-B1 cDNA. Ligand expression was verified by immunoblotting (not shown). EphB6 receptor expressing cells were overlaid on cells transfected with ephrin-B1, ephrin-A1 or empty vector, and co-incubated for an hour at 37° C. The EphB6 receptor was then precipitated with anti-myc and immunoblotted with anti-phosphotyrosine antibody. Stimulation of EphB6 with ephrin-B1-expressing cells resulted in a major increase in EphB6 tyrosine phosphorylation, while co-incubation with ephrin-A1-expressing or control cells had no effect (FIG. 1A). The increase in EphB6 receptor tyrosine phosphorylation caused by co-incubation with ephrin-B1-expressing cells was also observed upon transfection of NIH 3T3 fibroblasts and HEK 293 human embryonic kidney cells (FIG. 1B), indicating the effect was not cell specific. Stimulation of EphB6 receptor tyrosine phosphorylation was both time and ligand concentration dependent (FIGS. 1C,D).

In contrast to soluble monomers of ephrin, which can inhibit Eph receptor signaling, dimerized or oligomerized forms can stimulate receptor autophosphorylation and signaling (Davis et al. (1994); Sakano et al. (1996)). A soluble dimerized form of the ephrin-B1 ligand was also found to induce EphB6 phosphorylation. Although recombinant murine ephrin-B1 was utilized, it induced EphB6 phosphorylation as effectively as membrane expressed human ephrin-B1. Moreover, this ephrin-B1 induced phosphorylation could be completely inhibited by the addition of soluble EphB6 receptor to the medium (FIG. 1E), strongly suggesting the existence of a direct interaction between ephrin-B1 and EphB6 receptor.

Example 2

To demonstrate that EphB6 is trans-phosphorylated upon hetero-oligomerization with catalytically active members of the Eph family, EphB6 receptor was coexpressed with human EphB1 receptor in COS-7 cells. The EphB1 receptor was found to be constitutively activated when overexpressed. EphB6 underwent significant tyrosine phosphorylation upon coepression with the EphB1 receptor, trans-phosphorylated in a manner analogous to ErbB-3 (FIG. 2A). In contrast, catalytically inactive EphB1 (K651Q, B1-KD) was unable induce EphB6 phosphorylation (FIG. 2b). In NIH 3T3 fibroblasts, where the basal activity of EphB1 was determined to be much lower than in 293 or COS-7 cells, EphB6 trans-phosphorylation occurred in a ligand dependent manner (FIG. 2C).

As EphB1 and EphB6 have essentially the same electrophoretic mobility, the observed phosphorylation of EphB6 could, however, be due to co-precipitating phosphorylated EphB1 in this over-expressing system. Therefore, to unambiguously distinguish between the two receptors, a myc-tagged truncated EphB1 receptor lacking 102 C-terminal residues was constructed, but with its kinase domain intact (B1-Tr). Like the wild type receptor, truncated EphB1 was constitutively tyrosine phosphorylated, but now clearly smaller than EphB6. Co-expression of truncated EphB1 also resulted in dramatically increased EphB6 phosphorylation (FIGS. 2D,E), demonstrating that EphB6 phosphorylation can be provided by a catalytically active EphB receptor and suggesting that ephrin-B1 induced EphB6 phosphorylation may similarly result from trans-phosphorylation.

Example 3

In RT-PCR analysis, we detected EphB6 expression in human thymocytes as well as in mature peripheral blood T cells and in the T cell line Jurkat (FIG. 3). Two catalytically active members of the Eph family, EphB1 and EphB2, were also found to be expressed throughout the T cell lineage, while EphA2 could only be detected in thymocytes. The persistent expression of EphB6 across the T cell lineage suggested it might be important both during differentiation and in mature T cell function.

Single cell suspensions of human thymocytes were stimulated with anti-CD3 for 10 minutes, the receptor immunoprecipitated with anti-EphB6 antibodies and blotted with anti-phosphotyrosine. Polyclonal antibodies to EphB6 were raised against a peptide from the extreme C-terminal of EphB6, a unique sequence not present in any other known Eph receptor (see Experimental Procedures). This efficiently immunoprecipitated and Western blotted myc-tagged EphB6 (not shown). While tyrosine phosphorylation of the EphB6 receptor itself was not detected in response to anti-CD3 stimulation, a tyrosine phosphorylated protein of approximately 115 kDa (pp115) was co-precipitated (FIG. 4A).

pp115 was the only highly tyrosine phosphorylated protein consistently associated with EphB6 and remained for at least 20 minutes after anti-CD3 stimulation (FIG. 4B). The electrophoretic mobility of pp115 appeared similar to that of the c-Cb1 proto-oncogene, which is highly phosphorylated after TCR/CD3 stimulation Tsygankov et al. (1996)) (FIG. 4C). Western blotting with anti-EphB6 revealed the presence of a band of the expected molecular weight in Cb1 immunoprecipitates, but not in immunoprecipitates of FAK or Vav (FIG. 4D). Preimmune serum control blotting was also negative. This association was not noticeably altered by addition of anti-CD3, indicating that TCR/CD3 stimulation primarily induced Cb1 phosphorylation, rather than increasing its recruitment to the EphB6 receptor. Cb1 is central to signaling pathways from many receptors, functioning as a regulator of receptor tyrosine kinase activity, through initiation of receptor ubiquitination, and inducibly binding a variety of signal transducing molecules (Tsygankov et al. (1996); Fournel et al. (1996); Lupher et al. (1996); Lupher et al. (1997); Lupher et al. (1998); Ota et al. (1997); Thien et al. (1999); van Leeuwen (1999); Lee et al. (1999); Levkowitz et al. (1998); Miyake et al. (1998)).

This was confirmed by co-expressing human Cb1 with either the EphB6 or EphB1 receptor in COS-7 cells. Cb1 appeared to specifically co-precipitate with EphB6, as association with the catalytically active receptor EphB1 coud not be detected (FIG. 4E). Stimulation with ephrin-B1 expressing cells did not alter the level of EphB6-Cb1 association, nor Cb1 tyrosine phosphorylation (not shown). To further characterize this interaction, the binding of two mutants of Cb1 to EphB6 were examined. The first, G306E (Cb1*) was initially identified as a mutation in the C.elegans Cb1 orthologue, sli-1 (Jongeward et al. (1995)) and causes loss of Cb1 binding to the ErbB1 and PDGF receptors by disruption of the Cb1 phosphotyrosine binding domain (Bonita et al. (1997); Thien et al. (1997)). The second, 70-Z Cb1 (Cb1**), isolated as an oncogene from a murine B cell line (Blake et al. (1991)), contains an internal 17 amino acid deletion in the Cb1 RING finger domain While the 70-Z mutation only slightly decreased Cb1 binding to the EphB6 receptor, the G306E point mutation completely abolished association (FIG. 4F); confirming the specificity of binding and drawing a parallel between Cb1 binding to the EGP and PDGF receptors and its association with EphB6.

Example 4

Co-expression of Zap-70 with EphB6 or EphB1 receptors in COS-7 cells revealed a selective downregulation of Zap-70 phosphorylation by EphB6 (FIG. 5A). The EphB6 receptor inhibited Zap-70 tyrosine phosphorylation, while no significant change was observed upon EphB1 co-expression. This effect was ligand responsive, as a further decrease in Zap-70 phosphorylation occurred upon incubation of EphB6 co-transfected cells with ephrin-B1 expressing cells (FIG. 5A). The induction of EphB6 receptor tyrosine phosphorylation by ephrin-B1 probably contributes to the inhibition of Zap-70 through increased recruitment of effector proteins to the receptor.

Stimulation of the TCR complex leads to Zap-70 kinase phosphorylation by the Fyn and Lck src-like tyrosine kinases and subsequent Zap-70 activation, primarily through phosphorylation of tyrosine residue 493 in the Zap-70 catalytic domain (Wange et al. (1995) Mege et al. (1996); Kong et al. (1996)). The removal of Y493 results in a level of Zap-70 phosphorylation essentially reflecting its own basal kinase activity. A Y493F Zap-70 mutant (Zap*) was constructed and while demonstrating significantly lower tyrosine phosphorylation than wild type, Y493F Zap-70 was unaffected by EphB6 co-expression (FIG. 5B). This suggested that EphB6 might specifically affect phosphorylation of tyrosine residues characteristic of activated Zap-70.

The ability of EphB6 to alter signaling in T cells was demonstrated as follows. Stable overexpression of the myc-tagged EphB6 receptor in the mature T cell line Jurkat (B6-J) (FIG. 5C) was established. The transfected EphB6 receptor appeared to be functional, undergoing tyrosine phosphorylation upon stimulation of transfected T-cells with ephrin-B1 (FIG. 5D). TCR surface expression on control and B6-J cells was found to be equivalent by staining with anti-CD3ε-FITC.

Zap-70 was immunoprecipitated from control and EphB6 transfected T cells and its phosphorylation status examined by Western blotting. In agreement with our previous results, expressing Y493F Zap-70 in 293 cells, the basal phosphorylation of Zap-70 was not significantly affected by EphB6 overexpression. However, the induction of Zap-70 phosphorylation in response to TCR/CD3 stimulation was strongly inhibited (FIG. 5E). The amount of phosphorylated CD3ζ chain associated with Zap-70 was also decreased by EphB6 overexpression (FIG. 5F). The src-family kinase Lck is primarily responsible for phosphorylation of the CD3ζ chain upon TCR stimulation and subsequently regulates Zap-70 recruitment to the CD3 receptor complex, in addition to its activation of Zap-70 by direct phosphorylation. Lck activation by the CD45 phosphatase is one of, if not the, earliest events following TCR ligation and Lck kinase activity was significantly elevated after 5 minutes anti-CD3 stimulation of the control Jurkat cells. However, Lck activation was constitutively inhibited in EphB6 overexpressing B6-J cells (FIGS. 6A,B). Ephrin-B1 treatment of anti-CD3 stimulated control cells also partially inhibited Lck activation, but had no further effect upon Lck in EphB6 overexpressing cells, either alone, or in then presence of anti-CD3. The absence of ligand effect in B6-J cells suggests that the basal activity of overexpressed EphB6 alone is sufficient to prevent Lck activation. In sum, these results indicate that the EphB6 receptor modulates TCR signaling, by regulating the tyrosine phosphorylation and activity of TCR-associated kinases.

Example 5

The EphB6 receptor could downregulate both Lck and Zap-70 kinases, suggesting that EphB6 inhibition of TCR mediated CD25 upregulation was demonstrated as follows. pcDNA3 control and B6-J Jurkat cells were stimulated with anti-CD3 and the EphB6 ligand ephrin-B1. The ligand had no effect upon resting control cells, and demonstrated only a small and variable inhibition of TCR mediated CD25 upregulation (see FIG. 7A). In contrast, overexpression of EphB6, although variably affecting the basal level of CD25 expression, completely inhibited the ability of TCR stimulation to induce CD25 upregulation (FIG. 7B). In parallel with the ability of EphB6 to inhibit lck activation, no further inhibition of CD25 expression was observed upon addition of the ephrin-B1 ligand.

Figure 8C:
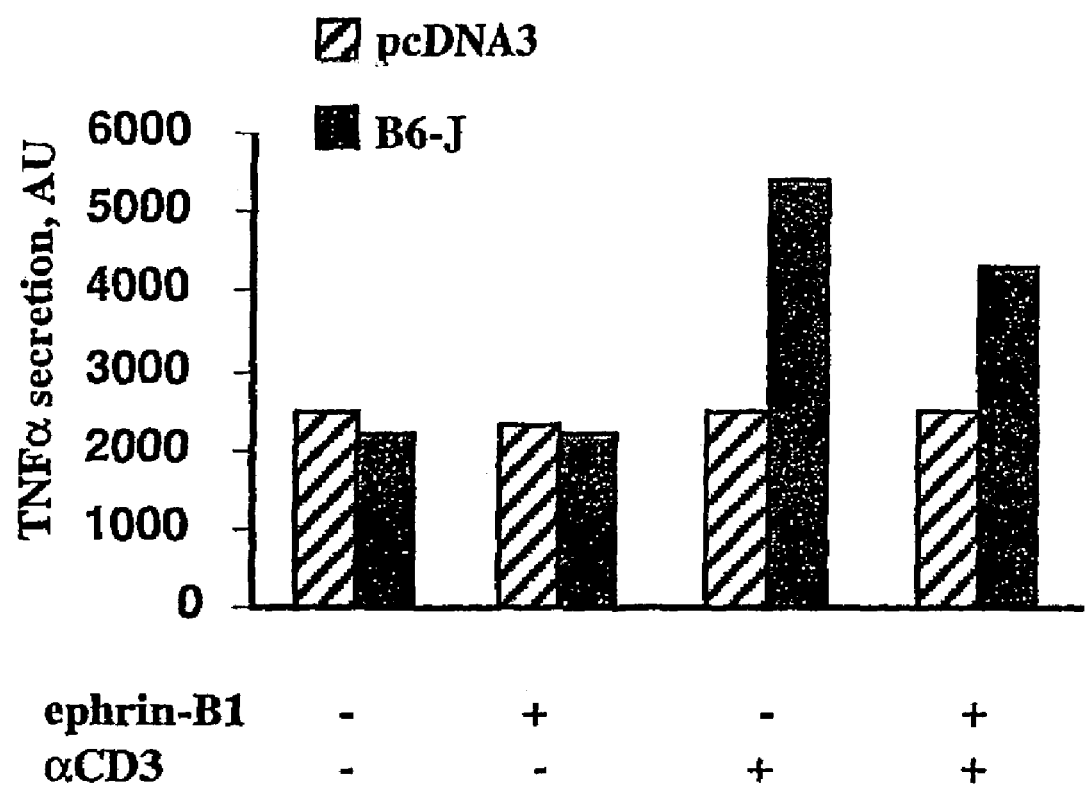
FIG. 8C is a further histogram illustrating the inhibition of CD25 regulation.

EphB6 is naturally highly expressed in thymocytes and when induction of CD25 in response to TCR activation was examined in these cells, ephrin-B1 co-stimulation caused a strong inhibition of CD25 upregulation, while ephrin-B1 alone had little effect (see FIG. 8C).

To confirm this role of endogenous EphB6, Jurkat cell lines overexpressing a dominant-negative form of EphB6, namely eliminating the cytoplasmic domain of the receptor (DN-J) were created. In contrast to overpression of wild type EphB6, the dominant-negative receptor did not prevent anti-CD3 mediated induction of CD25 expression and a further enhancement of anti-CD3 induced upregulation of CD25 was observed upon ephrin-B1 co-stimulation; presumably due to the removal of inhibitory input from the endogenous EphB6 receptor (see FIGS. 8A and 8B).

In summary, the results from Examples 1–5 provide support for methods of modulating T cells by suppressing antigen induced CD25 expression through manipulation of EphB6 receptors. The following Examples 6–8 further support methods of modulating the immune system through manipulation of EphB6 by demonstrating that modulation of EphB6 provides a method to modulate antigen induced cell death (AICD).

Discussion of Examples 1–5

Although the structure of EphB6 is typical of the EphB receptors, its kinase domain contains numerous alterations to critical catalytic residues and neither murine nor human EphB6 demonstrates kinase activity (Gurniak et al. (1996); Matsuoka et al. (1997)). Despite these structural abnormalities the human EphB6 receptor responds to ephrin-B1 stimulation by undergoing tyrosine phosphorylation. Further, the EphB6 tyrosine phosphorylation can be provided by a catalytically active partner, in particular, by the EphB1 receptor. While EphB1 receptor can trans-phosphorylate EphB6 upon co-transfection, in vivo EphB6 may potentially interact with multiple members of the EphB sub-family. Lacking catalytic activity, EphB6 is unlikely to operate as an independent receptor, but rather as part of a hetero-oligomeric complex with the active EphB receptors. Catalytically active EphB1 and EphB2 are both co-expressed with EphB6 throughout the T cell lineage, raising the possibility that EphB6 may interact with both receptors.

Until now, ErbB-3 of the EGF receptor family (Pinkas et al. (1996)) has been the only example of a trans-phosphorylated kinase-inactive receptor. However, without wanting to be bound by any particular theory, our findings suggest that this is a universal mechanism for signaling through catalytically inactive receptor tyrosine kinases. Two other kinase-inactive orphan receptors, Klg and Vik, (Chou et al. (1991); Hovens et al. (1992); Kelman et al. (1993); (Paul et al. (1992); Tamagnone et al. (1993); Stacker et al. (1993)) may signal in a similar manner and have catalytically active partners, as yet undescribed. ErbB-3 acts to modulate the intensity and duration of signaling by its active partner (Pinkas et al. (1996); Levkowitz et al. (1998)) and trans-phosphorylation results in recruitment of Shc and phosphatidylinositol 3-kinase specifically to the ErbB-3 receptor chain (Kim et al. (1994); Waterman et al. (1999)). In similar fashion, the catalytically inactive EphB6 receptor may recruit specific cytoplasmic signaling molecules, as Cb1 appears to specifically bind EphB6 and not an active EphB1 partner (FIG. 4E).

Unusually for a receptor tyrosine kinase, and particularly for an Eph receptor, EphB6 is most highly expressed in the thymus (Gurniak et al. (1996)). Several lines of evidence suggested a potential role for EphB6 in modulation of T-cell responses. First, several Eph family members interact with the src-like kinase Fyn (Choi et al. (1999); Ellis et al. (1996); Hock et al. (1998)), a TCR-associated kinase critical for the development of T-cell responses (Utting et al. (1998)). Secondly, Eph receptors can regulate re-organization of the actin cytoskeleton (Meima et al. (1997); Meima et al. (1997a)), an important event in TCR signaling; as disruption of actin with cytochalasin D or *Clostridium botulinum* toxin inhibits T lymphocyte responses to antigen (Valitutti et al. (1995). And finally, the Eph receptors can modulate integrin-mediated cell attachment (Becker et al. (2000); Huynh-Do et al. (1999)), integrins functioning as TCR co-receptors to modulate responses in both mature T cells and thymocytes (Abraham et al. (1999); Bleijs et al. (1999); Ticchioni et al. (1993); Wulfing and Davis (1998); Vivinus-Nebot et al. (1999)).

In accordance with this hypothesis, it was shown that both Zap-70 and Lck stimulation were decreased upon overexpression of EphB6 in T cells (FIGS. 5 and 6). EphB6 did not affect a Zap-70 mutant lacking the activating tyrosine 493 residue when co-pressed in COS-7 cells, appearing to prevent phosphorylation primarily of residues phosphorylated in the activated state. Therefore, decreased Zap-70 phosphorylation in COS-7 cells most likely reflects inhibition of endogenous src-family kinases; while in Jurkat, the primary inhibition of Lck activation by EphB6 is probably responsible for the absence of Zap-70 stimulation. This inhibition would reflect both a lack of phosphorylated CD3ζ chain to recruit Zap-70 to the signaling complex, and a decrease in the direct modification of Zap-70 by Lck. Without wishing to be bound by any particular theory, the decrease in TCR stimulated Lck kinase activity is in all probability the consequence of EphB6 induced re-arrangement of the cytoskeleton, sequestering lck away from the TCR/CD3 receptor complex. In support of our hypothesis, stimulation of β1-integrins with either soluble ligand or antibody has previously been shown to inhibit TCR mediated activation of Lck and Zap-70 (Mary et al. (1999)).

Inhibition of the early events of TCR signaling by overexpression of EphB6 was found to ultimately translate into an inhibition of T cell response, such as the induction of CD25 (IL-2Rα) expression Expression of CD25 is essential in the IL-2 driven clonal expansion that occurs upon exposure to antigen. Failure to express the high affinity IL-2R complex composed of the α, β and γ chains prevents the development of the necessary IL-2 autocrine proliferative loop. Thus without wishing to be bound by any one theory, one of the biological functions of EphB6, in conjunction with other EphB receptors, may be to control the clonal expansion of antigen activated T cells by suppressing antigen induced CD25 expression and associated events. Several alternative models of EphB6 function also become apparent. Under more physiological conditions, ligation of the EphB6 receptor may serve to maintain activation of the TCR signaling pathway below a certain threshold, preventing premature activation by inappropriate low affinity TCR interactions. Or, alternatively, the presence of varying ephrin-B ligands may modify the ability of T cells to respond to antigens presented on different cell-surfaces.

EphB6, like the ErbB1 and PDGF receptors, was found to physically associate with Cb1. The G315E mutation of the *C.elegans* Cb1 orthologue Sli-1 prevents interaction with the nematode ErbB protein (let-23) (Jongeward et al. (1995)) and the analogous Cb1 mutation disrupts binding to PDGF and ErbB-1 receptors (Bonita et al. (1997); Thien et al. (1997)). This mutation also abolished Cb1 association with EphB6 (FIG. 4F). The G306E mutation disrupts the Cb1 phosphotyrosine-binding domain, suggesting that phosphorylation of EphB6 or an intermediate docking protein may be important for Cb1 binding to the receptor. Although EGF stimulation of the ErbB-1 receptor induces tyrosine phosphorylation of Cb1 (Levkowitz et al. (1996)), increased Cb1 phosphorylation upon stimulation of the EphB6 receptor with ephrin-B1 (not shown) was not detected. This lack of Cb1 phosphorylation probably reflects the absence of EphB6 catalytic activity, suggesting that EphB6 may simply recruit Cb1 to the cell membrane, rather than modifying its function by phosphorylation. The failure to observe Cb1 phosphorylation upon ephrin-B1 stimulation also suggests that it is not a substrate of the catalytically active EphB6 partner. TCR/CD3 stimulation of T cells resulted in phosphorylation of EphB6-associated Cb1, although EphB6 itself did not undergo detectable phosphorylation, suggesting that Cb1 phosphorylation is probably mediated by TCR/CD3 associated cytoplasmic kinases.

The ability of Cb1 to bind EphB6 raises the possibility that EphB6 expression may be regulated by Cb1 mediated modification. It is now clear that Cb1 is responsible for the physical downregulation of many receptors through induction of receptor ubiquitination (Lee et al. (1999); Levkowitz et al. (1998); Miyake et al. (1998)). The addition of multiple ubiquitin moieties to the lysine residues of a protein targets it for degradation, either in cytoplasmic proteasomes or the lysosomal compartment (Hershko et al. (1998)). As all receptors binding to Cb1 undergo ubiquitination, it is likely that EphB6 will be similarly regulated. This activity of Cb1 is normally accompanied by its phosphorylation, suggesting that anti-CD3 induced phosphorylation of EphB6-associated Cb1 may trigger EphB6 downregulation (FIG. 8). While EphB6 may maintain activation of the TCR signaling pathway below a certain threshold, preventing premature responses to inappropriate stimulus, elimination of the inhibitory EphB6-Cb1 complex from the plasma membrane may be an obligatory event for maximal activation of the TCR signaling pathway.

To this point, Eph receptor function has been addressed primarily in the development and function of the nervous system, where they were shown to participate in targeting neurons and growth cones, as well as in synapse formation (Zhou et al. (1998); Flanagan et al. (1998)). This biological activity is essentially due to the ability of Eph receptors to reorganize the actin cytoskeleton and to control cell attachment by regulation of integrin receptors (Becker et al. (2000); Holland et al. (1997); Huynh-Do et al. (1999). Proper activation of T lymphocytes by antigen-presenting cells requires stimulation not only of the TCR, but the combined and coordinated engagement of its co-receptors. Most TCR co-receptors bind cell-surface ligands and are concentrated in areas of cell-cell contact, forming what has been termed an immunological synapse (Grakoui et al. (1999); Dustin et al. (1999)). Assembly of these synapses and subsequent T cell responses are strictly dependent upon cell attachment 101, actin cytoskeleton re-organization (Holsinger et al. (1998); Valitutti et al. (1995); Wulfing and Davis (1998)) and integrin receptor signaling (Abraham et al. (1999); Bleijs et al. (1999); Ticchioni et al. (1993); Wulfing et al. (1998); Vivinus-Nebot et al. (1999)). Without wishing to be bound by any particular theory, EphB receptors and in particular EphB6, may be involved in coordination of T cell attachment and formation of the immunological synapse and thus may be important modulators of both thymocyte selection and T-cell responses.

Example 6

To explore the potential role of EphB6 in regulation of AICD, we generated stable expression of myc-tagged human EphB6 in the mature T cell line Jurkat (FIG. 9A); a commonly used model of pre-stimulated mature T cells in AICD studies. AICD was induced in EphB6 and control pcDNA3 transfected cells by overnight stimulation with immobilized anti-CD3 antibody. To activate the EphB6 receptor, cells were also treated with the EphB6 ligand, ephrin-B1. Stable overexpression of the EphB6 receptor was found to significantly enhance TCR-mediated apoptosis in a ephrin-B1-dependent manner (FIG. 9B), thus confirming its potential to regulate the induction of AICD.

Example 7

Figure 10:
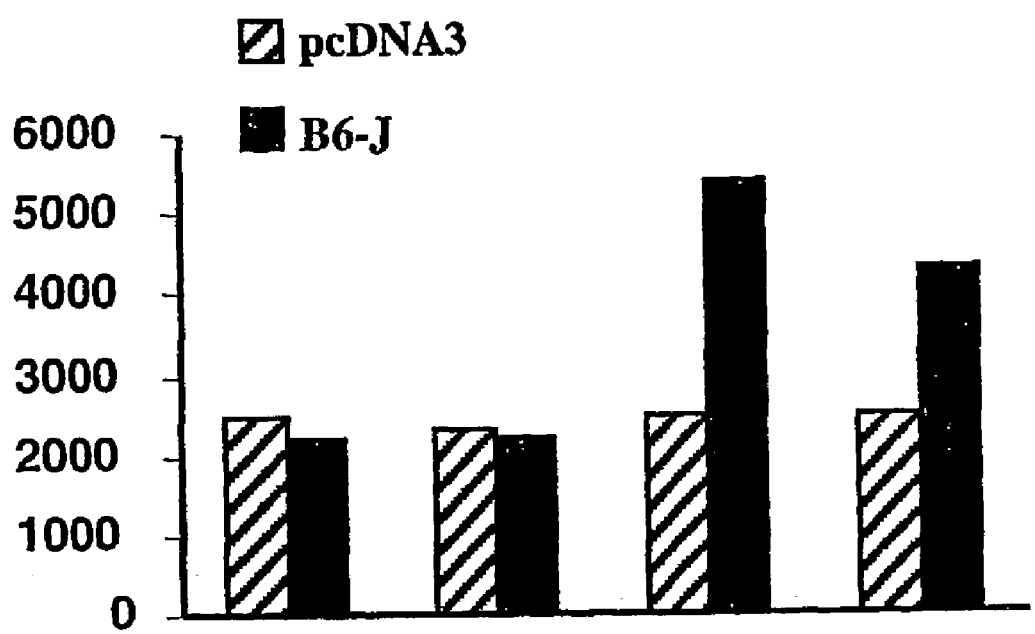
FIG. 10A is a histogram illustrating the EphB6-dependent increase in expression of TNFα.

Active T cell apoptosis is driven by the antigen-induced expression of the FASL and TNF death cytokines. In resting cells, both FAS-L and TNF are weakly induced by TCR stimulation, but in pre-activated cells these cytokines are highly expressed upon stimulation. In vitro experiments suggest that $CD4^+$ cells are primarily eliminated by FAS-L, while AICD of CD8 cells is predominantly triggered by TNF. We therefore examined the production of TNF by the control and EphB6 overexpressing $CD4^+$ jurkat cells. Ephrin-B1 alone did not induce TNF product nor did it significantly alter the response to anti-CD3. Anti-CD3 stimulation induced significant TNF production in EphB6 overexpressing Jurkat but not in control cells (FIG. 10). Thus, the increased apoptosis observed in EphB6 overexpressing cells may be due in part to increased TNF production.

Example 8

TNF efficiently activates both TNFR-I and TNFR-II. However, previous studies have suggested that only TNFR-I is coupled to a caspase cascade (Kozlosky et al. (1995)) and thus it may be the predominant transmitter of the TNF apoptic signal (Daniel et al. (1996); O'Leary and Wilkinson (1999)). We therefore examined the expression of the two TNF receptors an EphB6 and control Jurkat cells. Expression of TNFR-II, but not of TNFR-I, was suppressed upon incubation of both control and EphB6 overexpressing cells with ephrin-B1 (FIG. 11). Activation of the TCR overrode this effect in control cells, maintaining high TNFR-II expression despite ephrin-B1 stimulation. However, overexpression of EphB6 maintained the ephrin-B1-induced down regulation of TNFR-II in the presence of anti-CD3 stimulation. Interestingly, anti-CD3 stimulation of EphB6 overexpressing cells also reduced TNFR-II expression, while it had no effect upon the receptor in control cells. This is probably responsible for the greater degree of anti-CD3 induced apoptosis observed in EphB6 overexpressing cells and suggests that the basal activity of the EphB6 receptor is sufficient to make the cells more sensitive to the induction of apoptosis. Activation of the EphB6 receptor by ephrin-B1 co-stimulation with anti-CD3 resulted in a further decrease in TNFR-II expression, which is reflected in an increase in induction of apoptosis.

Figure 12:
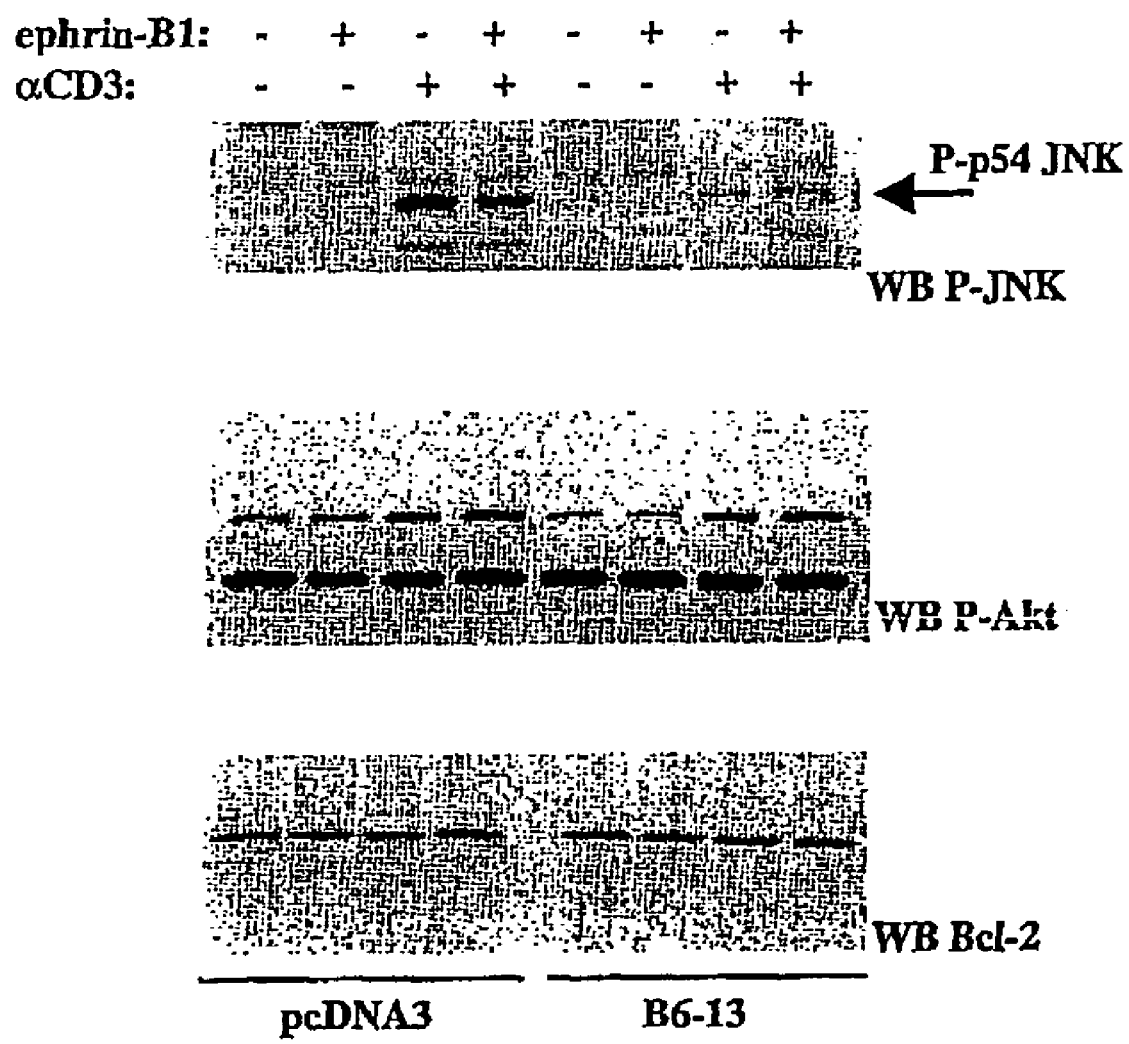
FIG. 12 are immunoblots illustrating that EphB6 receptor is able to prevent activation of p54 JNK.

TNFR-I and TNFR-II employ only partially distinct signaling pathways, both initiating the n-terminal JUN kinase cascade (Kozlosky et al. (1995)). Activation of the JNK pathway is required to protect cells from TNF-mediated apoptosis (Adams et al. (1999); Wang et al. (1998)). We examined the influence of EphB6 upon the JNK cascade by following the threonine-tyrosine phosphorylation (Thr183/Tyr185) of JNK upon anti-CD3 and ephrin-B1 stimulation. Overexpression of EphB6 not only resulted in an alteration in the balance of TNFR expression in favor of TNFR-I, but it also strongly inhibited long-term anti-CD3 induced JNK stimulation (FIG. 12). This effect was highly specific, as none of the other potentially anti-apoptic pathways examined, including AKT activation and Bcl-2 expression, was affected. the suppression of JNK activation appeared to be ligand-independent, suggesting that the basal activity of overexpressed EphB6 was sufficient for JUN kinase inhibition. the elimination of JNK-JUN signaling was previously reported to enhance TNF-induced apoptosis (Adams et al. (1999); Wang et al. (1998)), suggesting that the selective inhibition of the JUN kinase pathway observed here could further the promotion of AICD by EphB6.

Interestingly, while addressing the role of EphB6 in apoptosis, we observed that overexpression of a dominant negative form of EphB6 (cytoplasmic domain deleted) also increased the induction of AICD. This is surprising in light of the ability of wild type EphB6 to also promote AICD and probably reflects the ability of the DN receptor to enhance TCR mediated responses, as observed when examining CD25 expression. While not wishing to be bound by any particular theory, this presumably as the result of removing TCR inhibitory input from the endogenous EphB6 receptor. However, this effectively overrides the actual inhibition of EphB6-specific apoptic effects, such as TNFR modulation and TNF production, by the dominant negative receptor. While the apoptic contribution of the endogenous EphB6 receptor is removed, apoptosis still appears to increase due increased sensitivity to induction through the TCR.

In sum, our findings conclusively demonstrate that the EphB6 receptor serves an important role as a TCR co-receptor in the induction of AICD in mature activated T cells. Although driven by different factors to AICD, and proceeding via a different mechanism, the negative selection of thymocytes is also predominantly a TCR induced apoptic process. As the EphB6 receptor is strongly expressed in thymocytes, it is therefore likely that it also has an important role in regulating negative selection.

Materials and Methods for Examples 6–8

Western Blotting

Cells were quickly resuspended in ice cold lysis buffer consisting of 50 mM Tris-HCl pH 7.5, 150 mM NaCl, 10% glycerol, 1% Triton X-100, 1 mM ethylene glycol-bis (β-aminoethylether)-N,N,N'-N'-tetraacetic acid (EGTA), 10 µg/ml leupeptin, 10 µg/ml aprotinin, 1 mM PMSF, 1 mM Na-orthovanadate and 50 mM NaF. After solubilization an ice for 15 minutes, debris was removed by centrifugation at 12,000 g for 10 minutes at 4° C. and SDS sample buffer added. Samples were separated on SDS-polyacrylamide gels and transferred to nitrocellulose membranes (Amersham, Arlington Heights, Ill.). Membranes were blocked overnight at 4° C. with 7% blotting grade non-fat milk (Biorad, Richmond, Calif.) in PBS. Immunoblotting antibodies were added at optimal dilutions in PBS-T or TBS-T (0.1% Tween-20) and incubated at 4° C. overnight. After extensive washing with PBS-T, bound antibodies were detected using horseradish-peroxidase conjugated donkey anti-rabbit or sheep anti-mouse antibodies (Amersham, Arlington Heights, Ill.) and LumiGlo chemiluminescent reagents (Kirkegaard and Perry, Mass.).

Subcloning of EphB6 cDNA for EphB6 was cloned from normal human thymocyte RNA by RT-PCR into the expression vector pcDNA3 (Invitrogen, Calif.) and sequenced. Myc-tagged version of EphB6 was generated by insertion of an in frame Myc tag and construct verified by sequencing. Expression of the tagged protein was examined by transfection in COS-7 cells and Western blotting with appropriate antibodies.

EphB6 Stable Expression

To raise stable EphB6 expressing cells, the mature human T-cell line Jurkat was transfected with empty pcDNA3 or EphB6-M. The jurkat cells were electroporated in 400 µl complete RPMI medium with 30 µg of DNA by pulsing once for 65 msec at 260 V (BTK electro square porator, BTX Division of Genetronics Inc, San Diego, Calif.). Cells were incubated at 37° C. for 24 hours before addition of G418 to the medium. After 30 days of selection expression of the EphB6 receptor in resulting cell population was confirmed by immunoprecipitation with anti-Myc and western blotting with anti-Myc or anti-EphB6.

Stimulation of EphB6 Overexpressing and Control Cells

Soluble ephrin-B1-Fc fusion-protein dimers were purchased from R&D Systems (Minneapolis, Minn.). The dimeric ephrin-B1 fusion protein was pre-complexed with F(ab)'$_2$ goat anti-human Pc (Pierce) to form oligomers. F(ab)'$_2$ goat anti-human Fc was used as a control (no stimulation) where necessary. Although murine ephrin-B1 was used this effectively induced human EphB6 phosphorylation. Anti-CD3 (PharMingene, Canda) were immobilized on 24-well plates at 20 µg/ml for 4 hours at room temperatue, plates were rinsed are with PBS and cells stimulated for 24 hours, 37° C.

Analysis of TNFR I and TNFR II Expression by Flow Cytometry

EphB6 and pcDNA3 Jurkat cells were incubated in 0.5% serum for 24 hours with or without 5 µg/ml soluble oligomerized ephrin-B1 and immobilized anti-CD3 antibody. The expression of TNFα, TNFR I and TNFR II were then analyzed by staining with corresponding PE-labeled antibody and isotype control. Anti-TNFR-I and anti-TNFR II were from R&D Systems, MN.

Analysis of Apoptosis

Cells were resuspended in RPMI medium with 0.5% serum and supplements as indicated. After 24 hours incubation the percentage of apoptic cells was assessed by Annexin-V-FITC (Boehringer Mannheim, Indianapolis, Ind.) binding and Propidium iodide (PI) staining. Cells were analyzed on an Epics Elite V Flow Cytometer (Coulter Electronics).

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

Full Citations for References Referred to in the Specification

Abraham, C., Griffith, J. & Miller, J. The dependence for leukocyte function-associated antigen-1/ICAM-1 interactions in T cell activation cannot be overcome by expression of high density TCR ligand. *J Immunol* 162, 4399–405 (1999).

Adams, R. H. et al. Roles of ephrinB ligands and EphB receptors in cardiovascular development: demarcation of arterial/venous domains, vascular morphogenesis, and sprouting angiogenesis. *Genes Dev* 13, 295–306 (1999).

Aggarwal, S. S. Gollapudi, S. Gupta, J Immunol 162, 2154–61 (1999).

Alderson, M. R., et al., J Exp Med 181, 71–7 (1995).

Baker, S. J., E. P. Reddy, Oncogene 17, 3261–70 (1998).

Bartley T D, Hunt R W, Welcher A A, Boyle W J, Parker V P, Lindberg R A, Lu H S, Colombero A M, Elliott R L, Guthrie B A, et al. Nature 7 Apr. 1994;368(6471):558–60 B61 is a ligand for the ECK receptor protein-tyrosine kinase.

Becker, E. et al. Nck-interacting Ste20 kinase couples Eph receptors to c-Jun N-terminal kinase and integrin activation. *Mol Cell Biol* 20, 1537–45 (2000).

Blake, T. J., Shapiro, M., Morse, H. C. d. & Langdon, W. Y. The sequences of the human and mouse c-cbl proto-oncogenes show v-cb1 was generated by a large truncation encompassing a proline-rich domain and a leucine zipper-like motif. *Oncogene* 6, 653–7 (1991).

Blechman J M, Lev S, Brizzi M F, Leitner O, Pegoraro L, Givol D, Yarden Y, Biol Chem 1993 Feb. 25,268(6): 4399–406. Soluble c-kit proteins and antireceptor monoclonal antibodies confine the binding site of the stem cell factor.

Blechman J M, Lev S, Barg J, Eisenstein M, Vaks B, Vogel Z, Givol D, Yarden Y Cell 1995 Jan. 13,;80(1):103–13. The fourth immunoglobulin domain of the stem cell factor receptor couples ligand binding to signal transduction.

Bleijs, D. A., de Waal-Malefyt, R., Figdor, C. G. & van Kooyk, Y. Co-stimulation of T cells results in distinct IL-10 and TNF-alpha cytokine profiles dependent on binding to ICAM-1, ICAM-2 or ICAM-3. *Eur J Immunol* 29, 2248–58 (1999).

Boehme, S. A., L. Zheng, M. J. Lenardo, J Immunol 155, 1703–12 (1995).

Bohme, B. et al. Cell-cell adhesion mediated by binding of membrane-anchored ligand LERK-2 to the EPH-related receptor human embryonal kinase 2 promotes tyrosine kinase activity. *Journal of Biological Chemistry* 271, 24747–52 (1996).

Bonita, D. P., Miyake, S., Lupher, M. L., Jr., Langdon, W. Y. & Band, H. Phosphotyrosine binding domain-independent upregulation of the platelet-derived growth factor receptor alpha signaling cascade by transforming mutants of Cb1: implications for Cb1's function and oncogenicity. *Mol Cell Biol* 17, 4597–610 (1997).

Brambilla, R. et al. Membrane-abound LERK2 ligand can signal through three different Eph-related receptor tyrosine kinases. *Embo Journal* 14, 3116–26 (1995).

Chambers, C. A. & Allison, J. P. Co-stimulation in T cell responses. *Curr Opin Immunol* 9, 396–404 (1997).

Choi, S. & Park, S. Phosphorylation at Tyr-838 in the kinase domain of EphA8 modulates Fyn binding to the Tyr-615 site by enhancing tyrosine kinase activity. *Oncogene* 18, 5413–5422 (1999).

Chong, L. D., E. K. Park, E. Latimer, R. Friesel, I. O. Daar, Mol Cell Biol 20, 724–34 (2000).

Chou, Y. H. & Hayman, M. J. Characterization of a member of the immunoglobulin gene superfamily that possibly represents an additional class of growth factor receptor. *Proc Natl Acad Sci USA* 88, 4897–901 (1991).

Ciossek, T. & Ullrich, A. Identification of Elf-1 and B61 as high affinity ligands for the receptor tyrosine kinase MDK1. *Oncogene* 14, 35–43 (1997).

Ciossek. T. et al. Eph receptor-ligand interactions are necessary for guidance of retinal ganglion cell axons in vitro. *Eur J Neurosci* 10, 1574–80 (1998).

Cross, J. V., et al., J Biol Chem 274, 31150–4 (1999).

Daniel, T. O. et al. ELK and LERK-2 in developing kidney and microvascular endothelial assembly. *Kidney International Supplement* (1996).

Davis, S. et al. Ligands for EPH-related receptor tyrosine kinases that require membrane attachment or clustering for activity. *Science* 266, 816–9 (1994).

Dhein, J., H. Walczak, C. Baumler, K. M. Debatin, P. H. Krammer, Nature 373, 438–41 (1995).

Drescher, U. et al. In vitro guidance of retinal ganglion cell axons by RAGS, a 25 kDa tectal protein related to ligands for Eph receptor tyrosine kinases. *Cell* 82, 359–70 (1995).

Drescher, U. The Eph family in the patterning of neural development. [Review] [110 refs]. *Current Biology* 7(1997).

Durbin, L., et al., Development 127, 1703–13 (2000).

Dustin, M. L. & Shaw, A. S. Costimulation: building an immunological synapse [comment]. *Science* 283, 649–50 (1999).

Dutting, D., C. Handwerker, U. Drescher, Dev Biol 216, 297–311 (1999). Birgbauer, E., C. A. Cowan, D. W. Sretavan, H. Henkemeyer, Development 127, 1231–41 (2000).

Ellis, C. et al. A juxtamembrane autophosphorylation site in the Eph family receptor tyrosine kinase, Sek, mediates high affinity interaction with p59fyn. *Oncogene* 12, 1727–36 (1996).

Flanagan, J. G. & Vanderhaeghen, P. The ephrins and Eph receptors in neural development. *Annu Rev Neurosci* 21, 309–45 (1998).

Fournel, M., Davidson, D., Weil, R. & Veillette, A. Association of tyrosine protein kinase Zap-70 with the protooncogene product p120c-cb1 in T lymphocytes. *J Exp Med* 183, 301–6 (1996).

Friedman, G. C. & O'Leary, D. D. Eph receptor tyrosine kinases and their ligands in neural development. [Review] [72 refs]. *Current Opinion in Neurobiology* 6, 127–33 (1996).

Gale, N. W. et al. Eph receptors and ligands comprise two major specificity subclasses and are reciprocally compartmentalized during embryogenesis. *Neuron* 17, 9–19 (1996).

Gao, P. P., Yue, Y., Cerretti, D. P., Dreyfus, C. & Zhou, R. Ephrin-dependent growth and pruning of hippocampal axons. *Proc Natl Acad Sci USA* 96, 4073–7 (1999).

Geginat, J., Bossi, G., Bender, J. R. & Pardi, R. Anchorage dependence of mitogen-induced G1 to S transition in primary T lymphocytes. *J Immunol* 162, 5085–93 (1999).

Grakoui, A. et al. The immunological synapse: a molecular machine controlling T cell activation [see comments]. *Science* 285, 221–7 (1999).

Gurniak, C. B. & Berg, L. J. A new member of the Eph family of receptors that lacks protein tyrosine kinase activity. *Oncogene* 13, 777–86 (1996).

Hattori, M., M. Osterfield, J. G. Flanagan, Science 289, 1360–5 (2000).

Helbling, P. M., D. M. Saulnier, A. W. Brandli, Development 127, 269–78 (2000)

Hock, B. et al. Tyrosine-614, the major autophosphorylation site of the receptor tyrosine kinase HEK2, functions as multi-docing site for SH2-domain mediated interactions. *Oncogene* 17, 255–260 (1998).

Holland, S. J. et al. Juxtamembrane tyrosine residues couple the Eph family receptor EphB2/Nuk to specific SH2 domain proteins in neuronal cells. *Embo J* 16, 3877–88 (1997).

Holsinger, L. J. et al. Defects in actin-cap formation in Vav-deficient mice implicate an actin requirement for lymphocyte signal transduction. *Curr Biol* 8, 563–72 (1998).

Honegger, A. M., Schmidt, A., Ullrich, A. & Schlessinger, J. Evidence for epidermal growth factor (EGF)-induced intermolecular autophosphorylation of the EGF receptors in living cells. *Molecular & Cellular Biology* 10, 4035–44 (1990).

Hornberger, M. R. et al. Modulation of EphA receptor function by coexpressed ephrinA ligands on retinal ganglion cell axons. *Neuron* 22, 731–42 (1999).

Hopp, T. P. & Woods, K. R. Prediction of protein antigenic determinants from amino acid sequences. *Proc Natl Acad Sci USA* 78, 3824–8 (1981).

Hovens, C. M. et al. RYK, a receptor tyrosine kinase-related molecule with unusual kinase domain motifs. *Proc Natl Acad Sci USA* 89, 11818–22 (1992).

Hsueh, Y. P. & Sheng, M. Eph receptors, ephrins, and PDZs gather in neuronal synapses [comment]. *Neuron* 21, 1227–9 (1998).

Hunter, S., Burton, E. A., Wu, S. C & Anderson, S. M. Fyn associates with Cb1 and phosphorylates tyrosine 731 in Cb1, a binding site for phosphatidylinositol 3-kinase. *J Biol Chem* 274, 2097–106 (1999).

Huynh-Do, U. et al. Surface densities of ephrin-B1 determine EphB1-coupled activation of cell attachment through alphavbeta3 and alpha5beta1 integrins. *Embo J* 18, 2165–73 (1999).

Janeway, C. A., Jr. & Bottomly, K. Signals and signs for lymphocyte responses. *Cell* 76, 275–85 (1994).

Jongeward, G. D., Clandinin, T. R. & Sternberg, P. W. sli-1, a negative regulator of let-23-mediated signaling in C. elegans. *Genetics* 139, 1553–66 (1995).

Ju, S. T., et al., Nature 373, 444–8 (1995).

Kashles, O., Yarden, Y., Fischer, R., Ullrich, A. & Schlessinger, J. A dominant negative mutation suppresses the function of normal epidermal growth factor receptors by heterodimerization. *Molecular & Cellular Biology* 11, 1454–63 (1991).

Kavanaugh, W. M., Turck, C. W. & Williams, L. T. PTB domain binding to signaling proteins through a sequence motif containing phosphotyrosine. *Science* 268, 1177–9 (1995).

Kelman, Z., Simon-Chazottes, D., Guenet, J. L. & Yarden, Y. The murine vik gene (chromosome 9) encodes a putative receptor with unique protein kinase motifs. *Oncogene* 8, 37–44 (1993).

Kim, H. H., Sierke, S. L. & Koland, J. G. Epidermal growth factor-dependent association of phosphatidylinositol 3-kinase with the erbB3 gene product. *J Biol Chem* 269, 24747–55 (1994).

Koch, C. A., Anderson, D., Moran, M. F., Ellis, C., & Pawson, T. SH2 and SH3 domains: elements that control interactions of cytoplasmic signaling proteins. *Science* 252, 668–74 (1991).

Kong, G. et al. Distinct tyrosine phosphorylation sites in ZAP-70 mediate activation and negative regulation of antigen receptor function. *Mol Cell Biol* 16, 5026–35 (1996).

Kozlosky, C. J. et al. Ligands for the receptor tyrosine kinases hek and elk: isolation of cDNAs encoding a family of proteins. *Oncogene* 10, 299–306 (1995).

Krull, C. E. et al. Interactions of Eph-related receptors and ligands confer rostrocaudal pattern to trunk neural crest migration. *Current Biology* 7, 571–80 (1997).

Lee, P. S. et al. The Cb1 protooncoprotein stimulates CSF-1 receptor multiubiquitination and endocytosis, and attenuates macrophage proliferation. *Embo J* 18, 3616–28 (1999).

Lev S, Blechman J, Nishikawa S, Givol D, Yarden Y. Mol Cell Biol 1993 April ;13(4):2224–34. Interspecies molecular chimeras of kit help define the binding site of the stem cell factor.

Levkowitz, G. et al. c-Cb1/Sli-1 regulates endocytic sorting and ubiquitination of the epidermal growth factor receptor. *Genes Dev* 12, 3663–74 (1998).

Levkowitz, G. et al. Coupling of the c-Cb1 protooncogene product to ErbB-1/EGF-receptor but not to other ErbB proteins. *Oncogene* 12, 1117–25 (1996). 98. Hershko, A. & Ciechanover, A. The ubiquitin system. *Annu. Rev Biochem* 67, 425–79 (1998).

Lupher, M. L., Jr., Reedquist, K. A., Miyake, S., Langdon, W. Y. & Band, H. A novel phosphotyrosine-binding domain in the N-terminal transforming region of Cb1 interacts directly and selectively with ZAP-70 in T cells. *J Biol Chem* 271, 24063–8 (1996).

Lupher, M. L., Jr., Songyang, Z., Shoelson, S. E., Cantley, L. C. & Band, H. The Cb1 phosphotyrosine-binding domain selects a D(N/D)XpY motif and binds to the Tyr292 negative regulatory phosphorylation site of ZAP-70. *J Biol Chem* 272, 33140–4 (1997).

Lupher, M. L., Jr. et al. Cb1-mediated negative regulation of the Syk tyrosine kinase. A critical role for Cb1 phosphotyrosine-binding domain binding to Syk phosphotyrosine 323. *J Biol Chem* 273, 35273–81 (1998).

Mary, F. et al. Modulation of TCR signaling by beta1 integrins: role of the tyrosine phosphatase SHP-1. *Eur J Immunol* 29, 3887–97 (1999).

Matsuoka, H. et al. Expression of a kinase-defective Eph-like receptor in the normal human brain. *Biochemical & Biophysical Research Communications* 235, 487–92 (1997).

Mege, D. et al. Mutation of tyrosines 492/493 in the kinase domain of ZAP-70 affects multiple T-cell receptor signaling pathways. *J Biol Chem* 271, 32644–52 (1996).

Meima, L. et al. AL-1-induced growth cone collapse of rat cortical neurons is correlated with REK7 expression and rearrangement of the actin cytoskeleton. *Eur J Neurosci* 9, 177–88 (1997).

Meima, L., Moran, P., Matthews, W. & Caras, I. W. Lerk2 (ephrin-B1) is a collapsing factor for a subset of cortical growth cones and acts by a mechanism different from AL-1 (ephrin-A5). *Mol Cell Neurosci* 9, 314–28 (1997a).

Mellitzer, G., Xu, Q. & Wilkinson, D. G. Eph receptors and ephrins restrict cell intermingling and communication. *Nature* 400, 77–81 (1999).

Miao, H., E. Burnett, M. Kinch, E. Simon, B. Wang, Nat Cell Biol 2, 62–9 (2000). 113. Q. Xu, G. Mellitzer, V. Robinson, D. G. Wilkinson, Nature 399, 267–71 (1999).

Miao, H., Burnett, E., Kinch, M., Simon, E. & Wang, B. Activation of EphA2 kinase suppresses integrin function and causes focal-adhesion-kinase dephosphorylation. *Nat Cell Biol* 2, 62–9 (2000).

Miyake, S., Lupher, M. L., Jr., Druker, B. & Band, H. The tyrosine kinase regulator Cbl enhances the ubiquitination and degradation of the platelet-derived growth factor receptor alpha. *Proc Natl Acad Sci USA* 95, 7927–32 (1998).

Montschau, B. et al. Shared and distinct functions of RAGS and ELF-1 in guiding retinal axons. *Embo Journal* 16, 1258–67 (1997).

Nakamoto, M. et al. Topographically specific effects of ELF-1 on retinal axon guidance in vitro and retinal axon mapping in vivo. *Cell* 86, 755–66 (1996).

Noel, P. J., L. H. Boise, J. M. Green, C. B. Thompson, J Immunol 157, 636–42 (1996).

O'Leary, D. D. & Wilkinson, D. G. Eph receptors and ephrins in neural development *Curr Opin Neurobiol* 9, 65–73 (1999).

Ota, Y. & Samelson, L. E. The product of the proto-ocogene c-cbl: a negative regulator of the Syk tyrosine kinase. *Science* 276, 418–20 (1997).

Paul, S. R. et al. Molecular cloning of the cDNA encoding a receptor tyrosine kinase-related molecule with a catalytic region homologous to c-met *Int J Cell Cloning* 10, 309–14 (1992).

Pandey, A., Shao, H., Marks, R. M, Polverini, P. J. & Dixit, V. M. Role of B61, the ligand for the Eck receptor tyrosine kindase, in TNF-alpha-induced angiogenesis. *Science* 268, 567–9 (1995).

Park, S. & Sanchez, M. P. The Eek receptor, a member of the Eph family of tyrosine protein kinases, can be activated by three different Eph family ligands. *Oncogene* 14, 533–42 (1997).

Pasquale, E. B. The Eph family of Receptors. [Review] [57 refs]. *Current Opinion in Cell Biology* 9, 608–15 (1997).

Pindas, K. R. et al. Diversification of Neu differentiation factor and epidermal growth factor signaling by combinatorial receptor interactions. *Embo Journal* 15, 2452–67 (1996).

Roulston, A., C. Reinhard, P. Amiri, L. T. Williams, J Biol Chem 273, 10232–9 (1998).

Russell, J. H., B. Rush, C. Weaver, R. Wang, Proc Natl Acad Sci USA 90, 4409–13 (1993).

Sabapathy, K., et al., Curr Biol 9, 116–25 (1999).

Sakano, S. et al. Characterization of a ligand for receptor protein-tyrosine kinase HTK expressed in immature hematopoietic cells. *Oncogene* 13, 813–22 (1996).

Shimoyama, M. et al., Growth Factors 18, 63–78 (2000).

Smith, A., Robinson, V., Patel, K. & Wilkinson, D. G. The EphA4 and EphB1 receptor tyrosine kinases and ephrin-B2 ligand regulate targeted migration of branchial neural crest cells. *Current Biology* 7, 561–70 (1997).

Snapper, S. B. et al. Wiskott-Aldrich syndrome protein-deficient mice reveal a role for WASP in T but not B cell activation. *Immunity* 9, 81–91 (1998).

Songyang, Z. et al. SH2 domains recognize specific phosphopeptide sequences. *Cell* 72, 767–78 (1993).

Stacker, S. A. et al. Molecular cloning and chromosomal localisation of the human homologue of a receptor related to tyrosine kinases (RYK). *Oncogene* 8, 1347–56 (1993).

Takahashi, T., et al., Cell 76, 969–76 (1994).

Tamagnone, L. et al. The human ryk cDNA sequence predicts a protein containing two putative transmembrane segments and a tyrosine kinase catalytic domain. *Oncogene* 8, 2009–14 (1993).

Thien, C. B. & Langdon, W. Y. EGF receptor binding and transformation by v-cbl is ablated by the introduction of a loss-of-function mutation from the *Caenorhabditis elegans* sli-1 gene. *Oncogene* 14, 2239–49 (1997).

Thien, C. B., Bowtell, D. D. & Langdon, W. Y. Perturbed regulation of ZAP-70 and sustained tyrosine phosphorylation of LAT and SLP-76 in c-Cbl-deficient thymocytes. *J Immunol* 162, 7133–9 (1999).

Ticchioni, M. et al. Suppressive effect of T cell proliferation via the CD29 molecule. The CD29 mAb 1 "K20" decreases diacylglycerol and phosphatidic acid levels in activated T cells. *J Immunol* 151, 119–27 (1993).

Thoma, B., M. Grell, K. Pfizenmaier, P. Scheurich, J Exp Med 172, 1019–23 (1990).

Torres, R. et al. PDZ proteins bind, cluster, and synaptically colocalize with Eph receptors and their ephrin ligands [see comments]. *Neuron* 21, 1453–63 (1998).

Tsygankov, A. Y., Mahajan, S., Fincke, J. E. & Bolen, J. B. Specific association of tyrosine-phosphorylated c-Cbl with Fyn tyrosine kinase in T cells. *J Biol Chem* 271, 27130–7 (1996).

Ueno, H., Colbert, H., Escobedo, J. A. & Williams, L. T. Inhibition of PDGF beta receptor signal transduction by coexpression of a truncated receptor. *Science* 252, 844–8 (1991).

Utting, O., Teh, S. J. & Teh, H. S. T cells expressing receptors of different affinity for antigen ligands reveal a unique role for p59fyn in T cell development and optimal stimulation of T cells by antigen. *J Immunol* 160, 5410–9 (1998).

Valitutti, S., Dessing, M, Aktories, K., Gallati, H. & Lanzavecchia, A. Sustained signaling leading to T cell activation results from prolonged T cell receptor occupancy. Role of T cell actin cytoskeleton. *J Exp Med* 181, 577–84 (1995).

van der Geer, P., Hunter, T. & Lindberg, R. A. Receptor protein-tyrosine kinases and their signal transduction pathways. [Review] [468 refs]. *Annual Review of Cell Biology* 10, 251–337 (1994).

van Leeuwen, J. E., Paik, P. K. & Samelson, L. E. The Oncogenic 70Z Cbl Mutation Blocks the Phosphotyrosine Binding Domain-Dependent Negative Regulation of ZAP-70 by c-Cbl in Jurkat T Cells. *Mol Cell Biol* 19, 6652–6664 (1999).

Van Ostade, X., et al., Nature 361, 266–9 (1993).

Viola, A., Schroeder, S., Sakakibara, Y., & Lanzavecchia, A. T lymphocyte costimulation mediated by reorganization of membrane microdomains [see comments]. *Science* 283, 680–2 (1999).

Vivinus-Nebot, M. et al. Laminin 5 in the human thymus: control of T cell proliferation via alpha6beta4 integrins. *J Cell Biol* 144, 563–74 (1999).

Watanabe-Fukunaga, R., C. I. Brannan, N. G. Copeland, N. A. Jenkins, S. Nagata, Nature 356, 314–7 (1992).

Wang, H. U., Chen, Z. F. & Anderson, D. J. Molecular distinction and angiogenic interaction between embryonic arteries and veins revealed by ephrin-B2 and its receptor Eph-B4. *Cell* 93, 741–53 (1998).

Wange, R. L. et al. Activating and inhibitory mutations in adjacent tyrosines in the kinase domain of ZAP-70. *J Biol Chem* 270, 18730–3 (1995).

Waterman, H., Alroy, I., Strano, S., Seger, R. & Yarden, Y. The C-terminus of the kinase-defective neuregulin receptor ErbB3 confers mitogenic superiority and dictates endocytic routing. *Embo J* 18, 3348–58 (1999).

Winslow, J. W. et al. Cloning of AL-1, a ligand for an Eph-related tyrosine kinase receptor involved in axon bundle formation. *Neuron* 14, 973–81 (1995).

Wulfing, C. & Davis, M. M. A receptor/cytoskeletal movement triggered by costimulation during T cell activation. *Science* 282, 2266–9 (1998).

Wulfing, C., Sjaastad, M. D. & Davis, M. M. Visualizing the dynamics of T cell activation: intracellular adhesion molecule 1 migrates rapidly to the T cell/B cell interface and acts to sustain calcium levels. *Proc Natl Acad Sci USA* 95, 6302–7 (1998).

Xu, Q., Mellitzer, G., Robinson V. & Wilkinson, D. G. In vivo cell sorting in complementary segmental domains mediated by Eph receptors and ephrins. *Nature* 399, 267–71 (1999).

Yarden, Y. & Schlessinger, J. Epidermal growth factor induces rapid, reversible aggregation of the purified epidermal growth factor receptor. *Biochemisty* 26, 1443–51 (1987).

Yarden, Y. & Schlessinger, J. Self-phosphorylation of epidermal growth factor receptor: evidence for a model of intermolecular allosteric activation. *Biochemistry* 26, 1434–42 (1987a).

Yue, Y. et al. Specification of distinct dopaminergic neural pathways: roles of the Eph family receptor EphB1 and ligand ephrin-B2. *J Neurosci* 19, 2090–101 (1999).

Zisch, A. H. & Pasquale, E. B. The Eph family: a multitude of receptors that mediate cell recognition signals. [Review] [35 refs]. *Cell & Tissue Research* 290, 217–26 (1997).

Zheng, L. et al., *Nature* 377, 348–51 (1995).

Zhou, R. The Eph family receptors and ligands. [Review] [181 refs]. *Pharmacology & Therapeutics* 77, 151–81 (1998).

Zou, J. X. et al. An Eph receptor regulates integrin activity through R-Ras. *Proc Natl Acad Sci USA* 96, 13813–8 (1999).

DETAILED FIGURE LEGENDS

FIG. 1. Tyrosine Phosphorylation of the EphB6 Receptor is Induced by Ephrin-B1 Ligand Stimulation.
(a) COS-7 cells transiently transfected with EphB6-M encoding expression vector (pcDNA3) were stimulated by co-incubation for 1 hour at 37° C. with COS-7 cells transfected with empty vector (−), ephrin-A1 (A1), or ephrin-B1 (B1) cDNAs in pcDNA3. Receptor phosphorylation was monitored by immunoblotting anti-Myc immunoprecipitates with anti-phosphotyrosine (PY). EphB6-M expression was determined by blotting with anti-Myc.
(b) HEK-293 and NIH 3T3 cells transiently expressing EphB6-M were co-incubated for 1 hour with ligand expressing HEK-293 or NIH 3T3 cells respectively and receptor tyrosine phosphorylation and expression levels determined as above.
(c) Time dependent phosphorylation of EphB6. EphB6-M-expressing COS-7 cells were co-incubated with ephrin-B1 transfected COS-7 cells for the indicated time periods. EphB6-M receptor phosphorylation and expression were determined as in (a).
(d) Ligand concentration dependent EphB6 phosphorylation. EphB6-M-expressing COS-7 cells were co-incubated for 1 hour with COS-7 cells transfected with 5 μg of pcDNA3 (−), or varying amounts of ephrin-B1-pcDNA3 (B1) as indicated.
(e) Soluble EphB6 receptor blocks ephrin-B1 induced EphB6 phosphorylation. Control (pcDNA3) or EphB6-M transfected cells were stimulated with 1 μg/ml soluble oligomerized ephrin-B1 (B1) in the presence (+B6-R) or absence of 5 μg/ml soluble EphB6 receptor for 30 minutes at 37° C. Cells were lysed by boiling in 1% SDS. Phosphorylation of the membrane expressed myc-tagged EphB6 receptor was examined by immunoprecipitation with anti-phosphotyrosine and Western blotting with anti-Myc.

Figure 2:
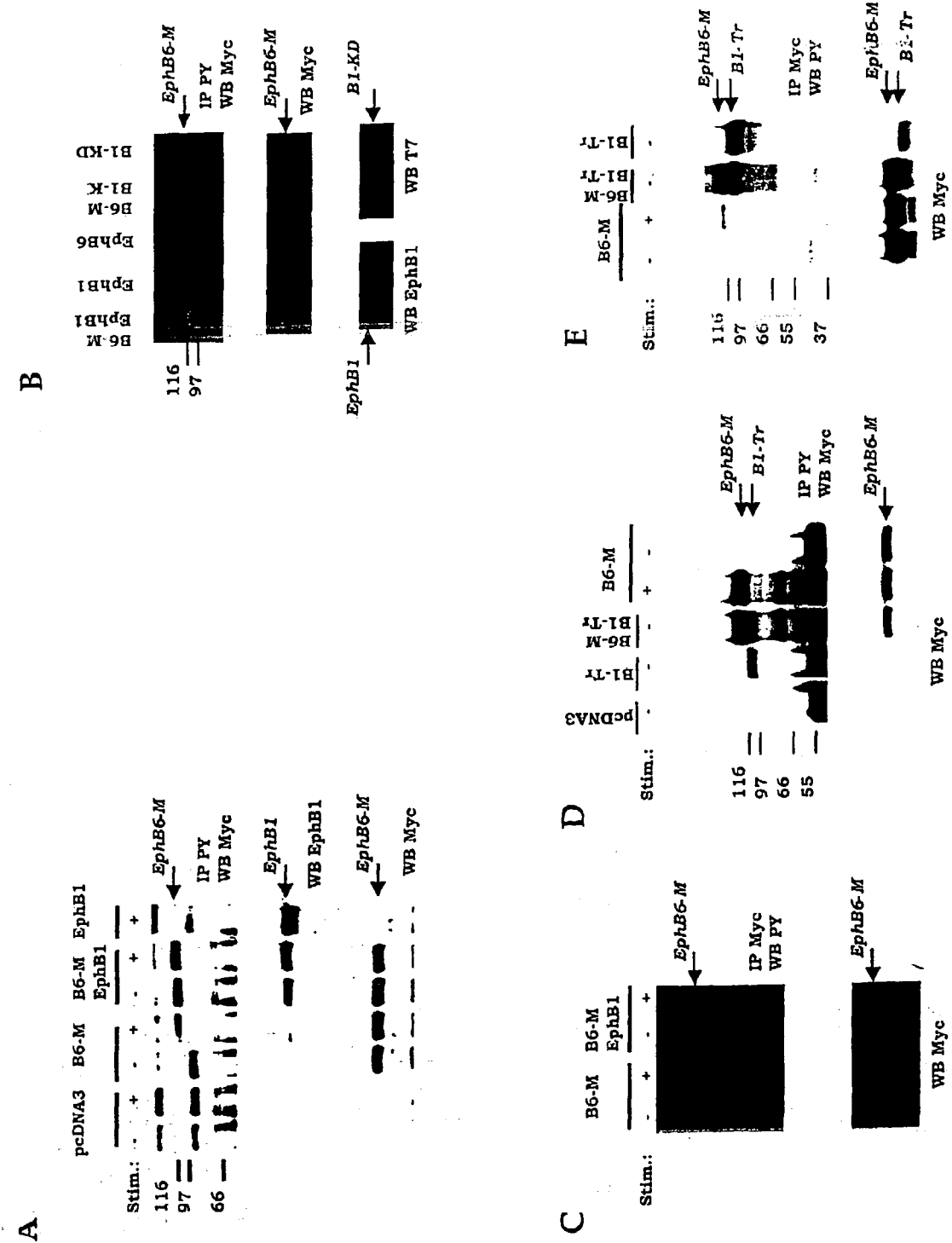
FIG. 2A is an immunoblot illustrating the phosphorylation of EphB6-M co-expression of EphB1 in COS-7 cells.
FIG. 2B is an immunoblot illustrating the phosphorylation of transfected EphB6-M co-transfected with EphB1 or T-7 tagged kinase inactive EphB1 (B1-KD).
FIG. 2C is an immunoblot illustrating the ligand dependent phosphorylation of EphB6-M.
FIG. 2D is an immunoblot illustrating the induction of EphB6 trans-phosphorylation by truncated EphB1.
FIG. 2E is another view of the immunoblot of FIG. 2D illustrating the induction of phosphorylation of EphB6 by truncated EphB1.

FIG. 2. EphB6 Receptor Phosphorylation is Induced by Co-expression of Catalytically Active EphB1 Receptor.
(a) COS-7 cells transiently transfected with either EphB1, EphB6-M (B6-M), or both receptors were co-incubated for 1 hour at 37° C. with control (−) or ephrin-B1 expressing (+) cells. Cells were lysed and immunoprecipitation performed with anti-phosphotyrosine. The presence of phosphorylated EphB6-M was detected by immunoblotting with anti-Myc. EphB1 and EphB6-M expression levels were quantitated by Western blotting with anti-EphB1 and anti-Myc, respectively.
(b) COS-7 cells were transiently transfected with EphB6-M (B6-M), EphB1, T-7 tagged kinase inactive EphB1 (B1-KD) or co-transfected with EphB6-M and EphB1 or B1-KD. After 72 hours the cells were lysed and immunoprecipitation performed with anti-phosphotyrosine. The presence of EphB6-M in immunoprecipitates was detected as in (a). Expression of the transfected proteins was examined by western blotting.
(c) NIH 3T3 cells were transiently transfected with EphB6-M alone, or in combination with EphB1. Cells were stimulated with 1 μg/ml of soluble oligomerized ephrin-B1, lysed and EphB6 receptor precipitated with anti-Myc. Phosphorylation of EphB6-M was monitored by immunoblotting with anti-phosphotyrosine.
(d) Truncated EphB1 receptor induces phosphorylation of EphB6. COS-7 cells transiently transfected with EphB6-M, truncated myc-tagged EphB1 (B1-Tr), or both receptors, were incubated for 1 hour with control (−) or ephrin-B1 ligand expressing (+) COS-7. Cells were lysed and precipitation with anti-phosphotyrosine performed. The presence of EphB6-M in immunoprecipitates and the EphB6-M expression level were determined by anti-Myc Western blot, as in (a).
(e) Eph6-M and B1-Tr were expressed in COS-7 cells as indicated and analyzed as in (c).

FIG. 3. Eph Receptor Expression in Human Thymocytes and T cells.
Expression of the EphA1, EphB1, EphB2 and EphB6 receptors was examined by RT-PCR in human thymocytes, peripheral blood T-lymphocytes and the mature T-cell line Jurkat. Control βactin primers were included in each reaction. The expected product sizes are: βactin—660 bp, EphA1—279 bp, EphB1—309 bp, EphB2—375 bp, EphB6—294 bp. The identity of the PCR products was confirmed by sequencing. Water controls (no DNA) were all negative (not shown). A 100 bp size ladder is shown on the right (Gibco, BRL).

FIG. 4. EphB6 Associates with c-Cb1.
(a) pp115 co-precipitates with EphB6 in human thymocytes. Thymocytes were stimulated with 1 μg/ml anti-CD3 in the presence of 5 μg/ml crosslinking antibody for 10 minutes. Cells were then lysed and precipitated with anti-EphB6 (358) or pre-immune serum (PI). Phosphorylated proteins in these complexes were detected by blotting with anti-phosphotyrosine. Preimmune (PI) antisera did not precipitate phosphorylated pp115.

(b) Time course of pp115 association with EphB6. Thymocytes were stimulated with anti-CD3 for the indicated time periods, precipitated with anti-EphB6 (358) and blotted with anti-phosphotyrosine.

(c) pp115 has the same electrophoretic mobility as c-Cb1. Thymocytes were stimulated with 1 μg/ml anti-CD3 in the presence of 5 μg/ml of crosslinking antibody for 10 min and Cb1 and EphB6 immunoprecipitated. Immunocomplexes were resolved by SDS PAGE, transferred to the nitrocellulose and blotted with anti-phosphotyrosine.

(d) Cb1, Vav, and FAK were immunoprecipitated from thymocyte lysates after anti-CD3 stimulation and immunocomplexes Western blotted with anti-EphB6 (358) or pre-immune serum as indicated.

(e) EphB6, but not EphB1, co-precipitates with Cb1. COS-7 cells were transiently transfected with Cb1 and EphB6-M (B6-M), or Cb1 and EphB1 as indicated. After 72 hours, Cb1 was precipitated and association with EphB6-M and EphB1 examined by blotting with anti-Myc and anti-EphB1 respectively.

(f) The G306E loss-of-function Cb1 mutant does not bind EphB6. COS-7 cells were transiently transfected with wild type Cb1, G306E Cb1 (Cb1*), or the oncogenic 70-Z Cb1 mutant (Cb1**), either alone or in combination with EphB6-M as indicated. After 72 hours EphB6-M association with Cb1 was examined by immunoblotting Cb1 immunoprecipitates with anti-Myc. Expression of each form of Cb1 and EphB6 was confirmed by Western blotting of cell lysates.

FIG. 5. EphB6 Downregulates the Zap-70 Kinase.

(a) EphB6 downregulates Zap-70 tyrosine phosphorylation. Zap-70 was transiently expressed in COS-7 cells, alone, or in combination with EphB6-M (B6-M) or EphB1 receptors. To activate EphB6, cells were incubated for 1 hour with ephrin-B1 ligand (+) expressing cells. Zap-70 phosphorylation was then analyzed by immunoblotting Zap-70 immunoprecipitates with anti-phosphotyrosine.

(b) Phosphorylation of Y493F Zap-70 is not altered by EphB6. Zap-70 or Y493F Zap-70 (Zap*) were expressed in COS-7 cells, alone, or with EphB6-M (B6-M. The phosphorylation status of Zap-70 and Zap* were analyzed by anti-phosphotyrosine blotting and expression by anti-Zap-70 blot. EphB6 expression was determined by Western blot of lysates.

(c,d) Transfected EphB6-M is tyrosine phosphorylated in Jurkat upon stimulation with ephrin-B1. The mature human T-cell line Jurkat was transfected with empty pcDNA3 or EphB6-M. After 30 days of Geneticin selection the resulting oligoclonal cell populations were screened by immunoprecipitation with anti-Myc and western blotting with anti-Myc or anti-EphB6 and the highest expressing cell population (B6J) selected. B6-J and pcDNA3 Jurkat cells were stimulated with 1 μg/ml soluble ephrin-B1 for 15 minutes at 37° C., cells lysed, EphB6-M immunoprecipitated with anti-Myc and its phosphorylation examined.

(e,f) Overexpression of EphB6 downregulates phosphorylation of Zap-70 and Zap-70 asssociated CD3ζ in Jurkat. Transfected Jurkat cells were stimulated 1 μg/ml soluble dimerized ephrin-B1 for 15 minutes at 37° C. and then costimulated for 7 minutes with 4 μg/ml anti-CD3. Zap-70 and CD3ζ tyrosine phosphorylation was then examined by anti-phosphotyrosine Western blotting of kinase immunoprecipitates. Results shown represent four independent experiments.

FIG. 6. The EphB6 Receptor Inhibits TCR Induced Activation of Lck.

(a,b) Lck immunoprecipitates were prepared from pcDNA3 and B6-J Jurkat cells stimulated as in FIG. 5e. Immunocomplexes were incubated in 50 μl of kinase buffer in the presence of 4 μg of the synthetic substrate peptide Raytide EL and γ[32P]-ATP for 15 min at room temperature. The kinase buffer containing the peptide was collected and loaded onto phosphocellulose paper. The paper was washed 3 times with 0.5% phosphoric acid and once with acetone, dried and counted in a β-counter. Results are shown in arbitrary units and represent one of four independent experiments. The presence of Lck was determined by immunoblotting of Lck immunoprecipitates run on non-reducing SDS PAGE with anti-Lck (not shown).

FIG. 7. EphB6 Overexpression Prevents TCR Mediated Upregulation of CD25.

(a,b) B6-J and pcDNA3 Jurkat cells were incubated in 0.5% serum for 24 hours with or without 5 μ/ml soluble oligomerized ephrin-B1 and immobilized anti-CD3 antibody as indicated. The expression of CD25 was then analyzed by staining with PE-labeled anti-CD25. The percentage of CD25 expressing cells is given in each case after subtraction of the isotype control.

FIG. 8. Endogenous EphB6 Downregulates CD25 Upregulation.

(A). Dominant negative (DN) EphB6 receptor expressing Jurkat cells (DN-J) were generated as in FIG. 4A. Expression of the DN receptor was assessed by Western Blot (see insert). DN-J cells were stimulated as in FIG. 7 and CD25 expression analyzed by flow cytometry. Results represent one of three independent experiments.

(B) A further view of dominant negative (DN) EphB6 receptor expressing Jurkat cells (DN-J) were generated as in FIG. 4A. Expression of the DN receptor was assessed by Western Blot (see insert). DN-J cells were stimulated as in FIG. 7 and CD25 expression analyzed by flow cytometry. Results represent one of three independent experiments.

(C). Purified thymocytes were starved for 24 hours, resuspended in 0.5% serum and stimulated with plate-immobilized anti-CD3 and ephrin-B1 as indicated. Expression of CD25 was analyzed by flow cytometry upon staining with PE-labeled anti-CD25 antibody. The percentage of CD25 expressing cells is given after subtraction of the isotype control. Results represent one of three independent experiments.

FIG. 9. The EphB6 receptor enhances TCR mediated apoptosis. a, Stable expression of EphB6 receptor. The mature T cell line Jurkat was transfected with empty pcDNA3 expression vector or myc-tagged EphB6. After 30 days of Geneticin selection EphB6 expression in the selected cells was confirmed by immunoprecipitation with anti-myc and blotting with either anti-myc or anti-EphB6. Equivalent expression of TCR/CD3 on EphB6 and control cells was confirmed by flow cytometry (not shown). b, EphB6 overexpressing (B6–13) and control pcDNA3 transfected cells were incubated in 0.5% serum for 24 hours with or without 5 μg/ml soluble oligomerized ephrin-B1 (B1) and immobilized anti-CD3 antibody as indicated. Induction of apoptosis was analyzed by annexin-V binding. The percentage of apoptic cells is given in each case. The results shown represent four independent experiments.

FIG. 10. The EphB6-dependent increase in activation induced cell death is accompanied by increased TNFα production EphB6 overexpressing and control Jurkat cells were stimulated for 24 hours as in FIG. 1. TNFα production was quantitated by chemiluminescent immunoassay of the cell culture supernatant.

FIG. 11. The EphB6 receptor inhibits expression of TNFR II but not TNFR I. Control (a) and EphB6 overexpressing (b) Jurkat T cells were stimulated as in FIG. 1 and expression of TNFR I and TNFR II determined by staining with PE-labeled anti-TNFR I or anti-TNFR II antibodies accordingly. TNFR I and TNFR II expression is given in arbitrary units (AU) after subtraction of the isotype control. The results shown represent three independent experiments.

FIG. 12. The EphB6 receptor prevents activation of p54 JNK. EphB6 and pcDNA3 control cells were stimulated as in FIG. 1. Cells were lysed, clarified by centrifugation and the lysates resolved by SDS PAGE. Phosphorylation of Jun kinase JNK) and Akt and expression of Bcl-2, were analyzed by Western Blotting with the appropriate antibody as indicated. The results shown represent three independent experiments.

Figure 13:
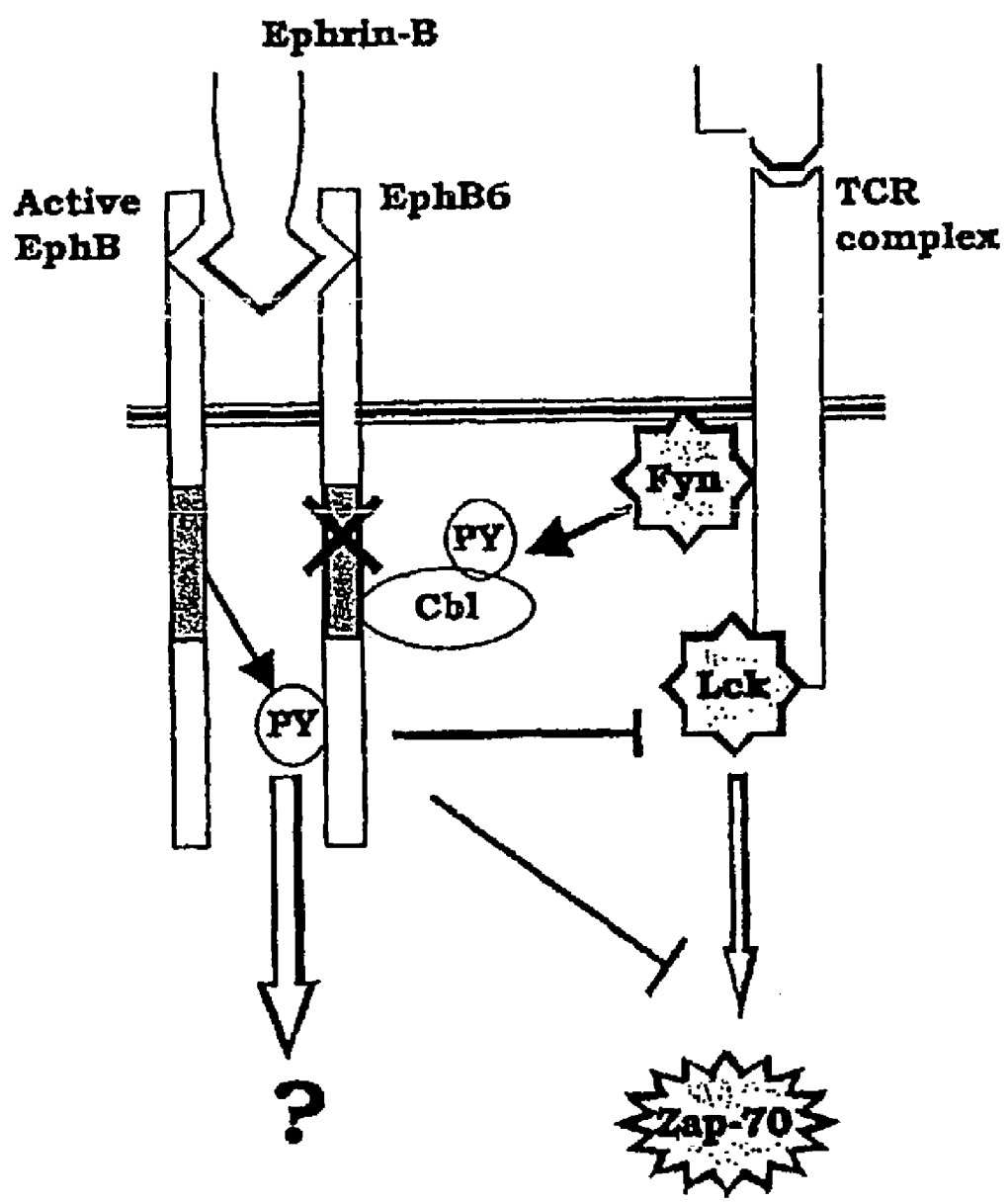
FIG. 13 provides an illustration of a model of EphB6 receptor interaction with the TCR signaling pathway.

FIG. 13. Model of EphB6 Receptor Interaction with the TCR Signaling Pathway. Binding of the transmembrane ephrin-B family ligand induces trans-phosphorylation of the catalytically inactive EphB6 receptor by its active EphB partner and brings the EphB6-Cb1 complex into the proximity of the T cell receptor. The recruitment of EphB6 to the immunological synapse downregulates activity of the TCR associated kinases Lck and Zap-70, possibly by affecting cytoskeleton and TCR complex formation. This raises the threshold for T cell activation, which may serve to prevent T cell activation by low-affinity TCR-antigen interaction. However, strong and sustained TCR stimulation causes phosphorylation of EphB6-associated Cb1, resulting in EphB6 ubqiutination (Ub) and consequent downregulation. The removal of EphB6 from the membrane allows complete activation o the TC signaling pathway and subsequently, of T cell responses.

We claim:

1. An in vitro method of inducing apoptosis comprising exposing a population of cells comprising T-cells to a composition comprising ephrin-B1, wherein said T-cells are exposed to said composition in the presence of anti-CD3 antibodies wherein said T-cells overexpress EphB6.

2. The method of claim 1 wherein the T-cells are human T-cells.

3. An in vitro method of inducing apoptosis comprising exposing T-cells to a composition comprising ephrin-B1 in the presence of anti-CD3 antibodies, wherein the T-cells overexpress EphB6.

* * * * *